United States Patent
Rusing et al.

(10) Patent No.: US 7,135,623 B1
(45) Date of Patent: Nov. 14, 2006

(54) **NUCLEIC ACID WHICH IS OBTAINED FROM *TETRAHYMENA* AND WHICH CODES FOR A DELTA-6-DESATURASE, THE PRODUCTION THEREOF AND USE**

(75) Inventors: Matthias Rusing, Cologne (DE); Thomas Kiy, Frankfurt am Main (DE); Annette Dominitzki, Klein-Winternheim (DE)

(73) Assignee: Nutrinova Nutrition Specialties & Food Engredients GmbH, Frankfurt am Main (DE)

( * ) Notice: Subject to any disclaimer, the term of this patent is extended or adjusted under 35 U.S.C. 154(b) by 232 days.

(21) Appl. No.: 10/070,666

(22) PCT Filed: Sep. 8, 2000

(86) PCT No.: PCT/EP00/08778

§ 371 (c)(1),
(2), (4) Date: Sep. 9, 2002

(87) PCT Pub. No.: WO01/20000

PCT Pub. Date: Mar. 22, 2001

(30) Foreign Application Priority Data

Sep. 10, 1999 (DE) ................................ 199 43 270

(51) Int. Cl.
*A01H 5/00* (2006.01)
*C12N 15/82* (2006.01)
*A01K 67/00* (2006.01)

(52) U.S. Cl. ........................ 800/298; 800/13; 800/281; 800/21; 435/320.1; 536/23.2

(58) Field of Classification Search ................ 536/23.2; 435/4, 320.1; 800/13, 298
See application file for complete search history.

(56) References Cited

U.S. PATENT DOCUMENTS 5,614,393 A * 3/1997 Thomas et al. ............. 435/134

OTHER PUBLICATIONS

Broun et al, Science 282: 1315-1317, Nov. 13, 1998.*
Van de Loo et al, PNAS, USA 92:6743-6747, Jul. 1995.*
Doerks et al, TIG 14(6): 248-250, Jun. 1998.*
Smith et al, Nature Biotechnology 15:1222-1223, Nov. 15, 1997.*
Brenner, S.E., TIG 15(4): 132-133, Apr. 1999.*
Bork et al, TIG 12(10): 425-427, Oct. 1996.*
DeLuca, V., AgBiotech News and Information 5(6): 225N-229N, 1993.*
Bertram, J., et al.: "Isolation of a Steroyl Coenzyme Desaturase From Tetrahymena Thermophila", Journal of Protozoology, vol. 28, No. 1, 1981, pp. 127-131 XP002152567.
Koll, M., et al.: "The Effect of Dietary Sterol on the Activity of Fatty Acid Desaturases Isolated From Tetrahymena-Setosa", Journal of Protozoology, vol. 37, No. 3, 1990, pp. 229-237, XP-002152568.
Fujiwara, Y., et al.: "Cytoplasmic Location of Linoleoyl-Coenzyme Desaturase in Microsomal Membranes of Rat Liver", Archives of Biochemistry and Biophysics, vol. 233, No. 2, 1984, pp. 402-407, XP002152569.
Napier, et al.: Identification of Caenorhabditis Elegans Delta6-Fatty-Acid-Desaturase by Heterologos Expression in Saccharomyces Cerevisiae, Biochemical Journal, GB, Portland Press, London, vol. 330 No. 2, Mar. 1998, pp. 611-614, XP002099453.
Database Genbank Accession No. AF031477 May 2, 1998, "Caenorhabditis Elegans Delta6-Fatty-Acid-Desaturase mRNA, complete cds".

* cited by examiner

*Primary Examiner*—Elizabeth F. McElwain
(74) *Attorney, Agent, or Firm*—Banner & Witcoff, Ltd.

(57) ABSTRACT

The invention relates to nucleic acid(s) which is/are obtained from tetrahymena and which code(s) for a ciliate-specific delta-6-desaturase that is involved in the biosynthesis of commercially valuable, multiply unsaturated fatty acids (so-called PUFA) polyunsaturated fatty acids). The inventive nucleotide sequence and the polypeptide sequence that can be obtained therefrom exhibit a surprisingly low sequence identity compared to other known natural desaturases. The invention also relates to the use of the nucleic acid(s) for overexpression in ciliates, preferably tetrahymena, in particular, *Tetrahymena thermophila*, with the aim of increasing the production of delta-6 unsaturated fatty acids, especially GLA.

23 Claims, 14 Drawing Sheets

Figure 2

Figure 1:
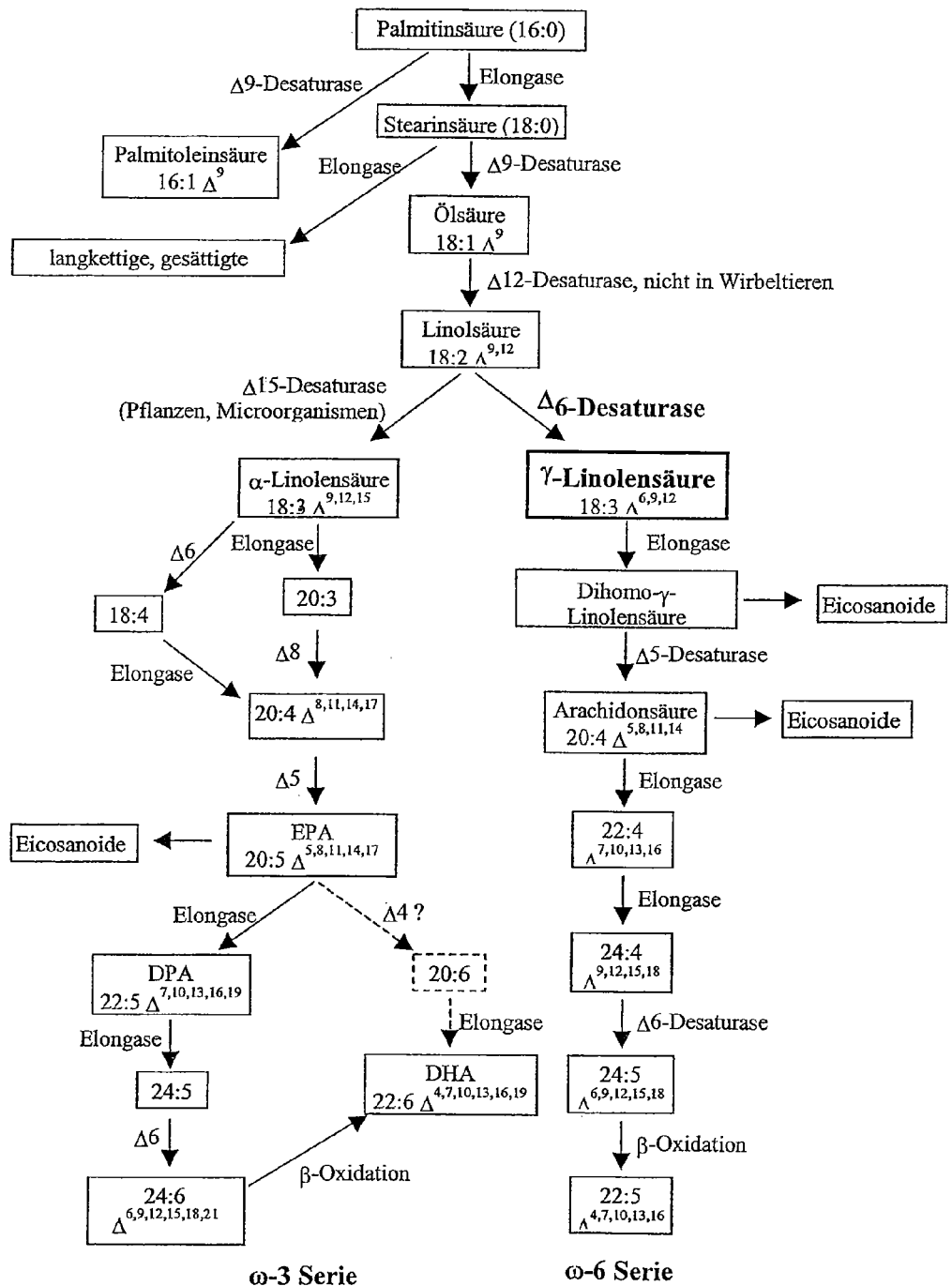

```
BLASTP 2.0.8 [Jan-05-1999]
Reference: Altschul, Stephen F., Thomas L. Madden, Alejandro A. Schaffer, Jinghui
Zhang, Zheng Zhang, Webb Miller, and David J. Lipman (1997), "Gapped BLAST and PSI-
BLAST: a new generation of protein database search programs", Nucleic Acids Res.
25:3389-3402.

Query= T.thermophila, delta-6-Desaturase  (352 letters)

Database: /LION/data/db/fast/nrdb
          387,705 sequences; 119,829,732 total letters Score      E
Sequences producing significant alignments:                       (bits)   Value trembl|AF078796|AF078796_1 gene: "des-5"; product: "delta 5 fat...    79    4e-14
trembl|AF031477|AF031477_1 product: "delta6-fatty-acid-desatura...    79    4e-14
trembl|Z81122|CET13F2_1 gene: "T13F2.1"; Caenorhabditis elegan...     78    1e-13
trembl|Z70271|CEW08D2_2 gene: "W08D2.4"; Caenorhabditis elegan...     78    1e-13
trembl|AF005096|AF005096_1 product: "desaturase/cytochrome b5 p...    70    3e-11
trembl|AJ222980|PPAJ2980_1 gene: "des6"; product: "delta6-acyl-...    69    6e-11
trembl|U79010|BOU79010_1 product: "delta 6 desaturase"; Borago...     67    2e-10
trembl|AC005397|AC005397_14 gene: "T3F17.14"; product: "putativ...    67    2e-10
trembl|AF007561|AF007561_1 product: "delta-6-Desaturase"; Bora...     66    4e-10
tremblnew|AF126799|AF126799_1 product: "delta-6 fatty acid desa...    64    2e-09
tremblnew|AF126798|AF126798_1 product: "delta-6 fatty acid desa...    63    3e-09
trembl|AF031194|AF031194_1 gene: "S276"; product: "S276"; Trit...     62    6e-09
tremblnew|AB021980|AB021980_1 product: "delta-6 fatty acid desa...    62    6e-09
tremblnew|AL078610|SCH35_12 gene: "SCH35.42c"; product: "putati...    62    8e-09
trembl|AJ224160|BNAJ4160_1 gene: "sld1"; product: "delta-8 sphi...    60    2e-08
trembl|AC004770|AC004770_2 product: "BC269730_2"; Homo sapiens...     60    3e-08
trembl|AJ224161|ATAJ4161_1 gene: "sld1"; product: "delta-8 sphi...    59    6e-08
tremblnew|AL050118|HSM800210_1 gene: "DKFZp586C201"; product: "...    57    2e-07
trembl|AB022097|AB022097_1 product: "delta 5 fatty acid desatur...    57    2e-07
trembl|X87143|HACYTB5RN_1 product: "cytochrome b5 containing fu...    50    2e-05
trembl|Y08460|MMMDES_1 gene: "Mdes"; product: "Mdes protein";  ...    50    3e-05
trembl|AF001394|AF001394_1 product: "fatty acid desaturase/cyto...    46    4e-04
trembl|AF002668|HSAF2668_1 product: "MLD"; Homo sapiens putati...     46    5e-04
swiss|Q08871|LLCD_SYNY3 LINOLEOYL-COA DESATURASE (EC 1.14.99.25...    43    0.003
```

Figure 3A

```
>aageneseq|W95504|W95504 Mortierella alpina delta 6 desaturase. Length =
457

Score =  89.7 bits (219), Expect = 4e-18
 Identities = 102/422 (24%), Positives = 152/422 (35%), Gaps = 88/422 (20%)

Query: 9   EIVLENKPELLNEYKFIYKDTEYDCTEYAKSNKHPGGLNFLNLFIDEKQDLTEYFRTLHS 68
           E + E K +   + I +  YD  E+     HPGG  L      +D T+ F T H
Sbjct: 19  EALNEGKKDAEAPFLMIIDNKVYDVREFVPD--HPGGSVILT---HVGKDGTDVFDTFHP 73

Query: 69  KQALKILKSFPKTGAKQEETE-SSKRFSILKKKLKHLFEPNWPIEIG----LFLTTFTLF 123
           + A + L +F       + + +  F+    +KL+ LF+     +         F +F L
Sbjct: 74  EAAWETLANFYVGDIDESDRDIKNDDFAAEVRKLRTLFQSLGYYDSSKAYYAFKVSFNLC 133

Query: 124 VTGCLT---QKW--------YFSIPLLVLMQIISGWIGHSMNHNRNPILR----KFALVY 168
           + G  T    KW           S   LL L   GW+ H   H++   R     F
Sbjct: 134 IWGLSTVIVAKWGQTSTLANVLSAALLGLFWQQCGWLAHDFLHHQVFQDRFWGDLFGAFL 193

Query: 169 APLCGGFSNKWWGRKHNQHHMFTNNILKDEDIQ-HDYKLWQ------------------ 208
           +C GFS+ WW   KHN HH   N   +D DI  H    W
Sbjct: 194 GGVCQGFSSSWWKDKHNTHHAAPNVHGEDPDIDTHPLLTWSEHALEMFSDVPDEELTRMW 253

Query: 209 ------------FP---FLFLKWKLDSIL--------------ASYYEFEGIFLALHWV 238
                       FP    F   L W L SIL                E +  LA+HW
Sbjct: 254 SRFMVLNQTWFYFPILSFARLSWCLQSILFVLPNGQAHKPSGARVPISLVEQLSLAMHWT 313

Query: 239 LLFNQNFYIV---------ILSELIAGFFSASILVGNHEN--EMKFERRITLPFFEHQI 286
             F +              ++S+ + G   A +   NH     + E + + FF   QI
Sbjct: 314 WYLATMFLFIKDPVNMLVYFLVSQAVCGNLLAIVFSLNHNGMPVISKEEAVDMDFFTKQI 373

Query: 287 AASRNYAFHDIFSLLIMGGMQYQTEHHFFPQIPFYRLPKARVIIAEELKKWNLKIHEGPI 346
             R+     +F+   GG+ YQ EHH FP +P +     K +  +    KK+N++ H +
Sbjct: 374 ITGRD-VHPGLFANWFTGGLNYQIEHHLFPSMPRHNFSKIQPAVETLCKKYNVRYHTTGM 432

Query: 347 FE 348
           E
Sbjct: 433 IE 434
```

Figure 3B

```
>trembl|AF031477|AF031477_1 product: "delta6-fatty-acid-desaturase";
Caenorhabditis elegans delta6-fatty-acid-desaturase mRNA, complete cds.
//:gp|AF031477|3088520 product: "delta6-fatty-acid-desaturase";
Caenorhabditis elegans delta6-fatty-acid-desaturase mRNA, complete cds.
Length = 443

Score = 79.2 bits (192), Expect = 4e-14
 Identities = 100/390 (25%), Positives = 132/390 (33%), Gaps = 95/390 (24%)

Query: 41   KHPGGLNFLNLFIDEKQDLTEYFRTLH--SKQALKILKSFPKTGAKQE--ETESSKR---  93
            KHPGG         D T F   H S QA K L    K G   E  E +   KR
Sbjct: 28   KHPGGAVIEQY---RNSDATHIFHAPHEGSSQAYKQLDLLKKHGEHDEFLEKQLEKRLDK  84

Query: 94   -------------------FSILKKKLKH--LFEPNWPIEIGLFLTTFTLFVTGCLTQ  130
                               F  L++KL    L + N +   ++T ++        Q
Sbjct: 85   VDINVSAYDVSVAQEKKMVESFEKLRQKLHDDGLMKANETYFLFKAISTLSIMAFAFYLQ 144

Query: 131  K--WYF-SIPLLVLMQIISGWIGHSMNHNR----NPILRKFALVYAPLCGGFSNKWWGRK 183
               WY  S  LL L   GW+ H  H +      P+   +L +    GFS   WW  K
Sbjct: 145  YLGWYITSACLLALAWQQFGWLTHEPCHQQPTKNRPLNDTISLFFGNFLQGFSRDWWKDK 204

Query: 184  HNQHHMFTNNILKDEDI--------------------------QHDYKLWQFPFLF 213
            HN HH  TN I  D DI                          QH Y    P L
Sbjct: 205  HNTHHAATNVIDHDGDIDLAPLFAFIPGDLCKYKASFEKAILKIVPYQHLYFTAMLPMLR 264

Query: 214  LKWKLDSILASYYE-------------FEGIFLALHWVLLFNQNFYI---------VILS 251
              W   S+   + E             +E +  HW +F Q F +           I+S
Sbjct: 265  FSWTGQSVQWVFKENQMEYKVYQRNAFWEQATIVGHWAWVFYQLFLLPTWPLRVAYFIIS 324

Query: 252  ELIAGFFSASILVGNHENEMKF--ERRITLPFFEHQIAASRNYAFHDIFSLLIMGGMQYQ 309
            ++  G  A ++   NH + K+    RI  F  QI +RN        L  GG+ YQ
Sbjct: 325  QMGGGLLIAHVVTFNHNSVDKYPANSRILNNFAALQILTTRNMTPSPFIDWL-WGGLNYQ 383

Query: 310  TEHHFFPQIPFYRLPKARVIIAEELKKWNL 339
            EHH FP +P  L        + E K+ NL
Sbjct: 384  IEHHLFPTMPRCNLNACVKYVKEWCKENNL 413
```

Figure 3C

```
>trembl|U79010|BOU79010_1 product: "delta 6 desaturase"; Borago
officinalis delta 6 desaturase mRNA, complete cds. //:gp|U79010|2062403
product: "delta 6 desaturase"; Borago officinalis delta 6 desaturase mRNA,
complete cds. Length = 448

Score = 67.1 bits (161), Expect = 2e-10
 Identities = 100/414 (24%), Positives = 154/414 (37%), Gaps = 100/414
(24%)

Query: 6     TQEEIVLENKPELLNEYKFIYKDTEYDCTEYAKSNKHPGGLNFLNLFIDEKQDLTEYFRT 65
             T +E+   +KP     +     +   YD +++ K HPGG  L        Q++T+ F
Sbjct: 10    TSDELKNHDKP---GDLWISIQGKAYDVSDWVKD--HPGGSFPLKSLAG--QEVTDAFVA 62

Query: 66    LHSKQALKILKSFPKTGAKQEE---TESSK---------RFSILKKKLKHLFEPNWPIE 112
             H    K L F TG   ++  +E SK          +  + KK   +F     I
Sbjct: 63    FHPASTWKNLDKF-FTGYYLKDYSVSEVSKDYRKLVFEFSKMGLYDKKGHIMFATLCFIA 121

Query: 113   IGLFLTTF-TLFVTGCLTQKWYFSIPLLVLMQIISGWIGHSMNHNR---NPILRKFALVY 168
             +  ++ +  LF G L    FS L+ + I SGWIGH  H    +   L KF ++
Sbjct: 122   MLFAMSVYGVLFCEGVLVH--LFSGCLMGFLWIQSGWIGHDAGHYMVVSDSRLNKFMGIF 179

Query: 169   APLC-GGFSNKWWGRKHNQHHMFTNNILKDEDIQH---------------------- 202
             A C  G S  WW   HN HH+  N++ D D+Q+
Sbjct: 180   AANCLSGISIGWWKWNHNAHHIACNSLEYDPDLQYIPFLVVSSKFFGSLTSHFYEKRLTF 239

Query: 203   --------DYKLWQFPFLFLKWKLDSILASY-----------YEFEGIFLALHWVLL- 240
                     Y+ W F +   +L+ + + S              +E G +   W L
Sbjct: 240   DSLSRFFVSYQHWTFYPIMCAARLNMYVQSLIMLLTKRNVSYRAHELLGCLVFSIWYPLL 299

Query: 241   ------FNQNFYIVILSELIAGF--------FSASILVGNHENEMKFERRITLPFFEHQ 285
                   + +    VI S + G          FS+S+ VG +    FE++ T       +
Sbjct: 300   VSCLPNWGERIMFVIASLSVTGMQQVQFSLNHFSSSVYVGKPKGNNWFEKQ-TDGTLDIS 358

Query: 286   IAASRNYAFHDIFSLLIMGGMQYQTEHHFFPQIPFYRLPKARVIIAEELKKWNL 339
             ++  FH         GG+Q+Q EHH FP++P   L K    + E  KK NL
Sbjct: 359   CPPWMDW-FH--------GGLQFQIEHHLFPKMPRCNLRKISPYVIELCKKHNL 403
```

Figure 3D

```
>tremblnew|AF126799|AF126799_1 product: "delta-6 fatty acid desaturase";
Homo sapiens delta-6 fatty acid desaturase mRNA, complete cds.
//:gp|AF126799|4406528 product: "delta-6 fatty acid desaturase"; Homo
sapiens delta-6 fatty acid desaturase mRNA, complete cds. Length = 444

Score = 63.6 bits (152), Expect = 2e-09
 Identities = 92/390 (23%), Positives = 152/390 (38%), Gaps = 88/390 (22%)

Query: 31   YDCTEYAKSNKHPGGLNFLNLFIDEKQDLTEYFRTLHSKQAL--KILK-----SFPKTGA 83
            Y+ T++  S +HPGG    +  + E D T+ FR  H      K LK
Sbjct: 44   YNITKW--SIQHPGGQRVIGHYAGE--DATDAFRAFHPDLEFVGKFLKPLLIGELAPEEP 99

Query: 84   KQEETESSK---RFSILKKKLK--HLFEPNWPIEIGLF--------LTTFTLFVTGCLTQ 130
            Q+ ++SK     F  L+K + +LF+ N    + L         + FT+F  G
Sbjct: 100  SQDHGKNSKITEDFRALRKTAEDMNLFKTNHVFFLLLLAHIIALESIAWFTVFYFGNGWI 159

Query: 131  KWYFSIPLLVLMQIISGWIGHSMNH------NRNPILRKFALVYAPLCGGFSNKWWGRK 183
              +  +L  Q  +GW+ H H        N ++ KF + +      G S  WW +
Sbjct: 160  PTLITAFVLATSQAQAGWLQHDYGHLSVYRKPKWNHLVHKFVIGHLK---GASANWWNHR 216

Query: 184  HNQHHMFTNNILKDEDIQ--HDYKL--WQPPFLFLKWKL----------------DSIL 222
            H QHH   N   KD D+  H + L  WQ P   + K KL                  ++
Sbjct: 217  HFQHHAKPNIFHKDPDVNMLEVFVLGEWQ-PIEYGKKKLKYLPYNHQHEYFFLIGPPPLLI 275

Query: 223  ASYYEFEGI--------FLALHWVLLFNQNFYIV------ILSELIAGFFSASILVGNH- 267
            Y++++ I          ++ L W + +  F+I         IL  L+  F +    +H
Sbjct: 276  PMYFQYQIIMTMIVHKNWVDLAWAVSYYIRFFITYIPFYGILGALL--FLNFIRFLESHW 333

Query: 268  --------ENEMKFERRITLPFFEHQIAASRNYA---FHDIFSLLIMGGMQYQTEHHFFP 316
                    M+ ++       +F  Q+ A+ N    F+D FS    G + +Q EHH FP
Sbjct: 334  FVWVTQMNHIVMEIDQEAYRDWFSSQLTATCNVEQSFFNDWFS----GHLNFQIEHHLFP 389

Query: 317  QIPFYRLPKARVIIAEELKKWNLKIHEGPI 346
            +P + L K  ++      K  ++  E P+
Sbjct: 390  TMPRHNLHKIAPLVKSLCAKHGIEYQEKPL 419
```

Figure 3E

```
>swiss|Q08871|LLCD_SYNY3 LINOLEOYL-COA DESATURASE (EC 1.14.99.25)
(DELTA(6)-DESATURASE).//:trembl|L11421|SSD6DS_1 product: "delta-6-
Desaturase"; Synechocystis sp. delta-6-Desaturase gene, complete cds.
//:trembl|D90914|SSD914_112 gene: "des6"; product: "delta-6-Desaturase";
Synechocystis sp. PCC6803 complete genome, 16/27, 1991550-2137258.
//:pironly|S35157|S35157 Delta(6)-desaturase - Synechocystis
sp.//:gp|D90914|1653589 gene: "des6"; product: "delta-6-Desaturase";
Synechocystis sp. PCC6803 complete genome, 16/27, 1991550-2137258.
//:gp|L11421|349563 product: "delta-6-Desaturase"; Synechocystis sp. delta-
6-Desaturase gene, complete cds. Length = 359

Score = 43.4 bits (100), Expect = 0.003
 Identities = 63/288 (21%), Positives = 101/288 (34%), Gaps = 61/288 (21%)

Query: 120 FTLFVTGCLTQKWYFSIPLLVLMQIISGWIGHSMNHNR---NP-ILRKFALVYAPLCGGF 175
           F LF     +   + L + +    S +GH  NHN   NP I R    + Y +   G
Sbjct: 57  FVLFAPVIFPVRLLGCMVLAIALAAFSFNVGHDANHNAYSSNPHINRVLGMTYDFV--GL 114

Query: 176 SNKWWGRKHNQ-HHMFTNNILKDEDIQHDYKLWQFPFL----------FLKWKLDSILAS 224
           S+ W  +HN  HH +TN +  D +I D  +   P              F  W L   +
Sbjct: 115 SSFLWRYRHNYLHHTYTNILGHDVEIHGDGAVRMSPEQEHVGIYRFQQFYIWGLYLFIPF 174

Query: 225 YYEFEGIFLAL-------HWVLLFNQNFYIVILS------------ELIAGFFSASILVG 265
           Y+    ++L L       H + F     +L            L GF   +L+G
Sbjct: 175 YWFLYDVYLVLNKGKYHDHKIPPFQPLELASLLGIKLLWLGYVFGLPLALGFSIPEVLIG 234

Query: 266 NHENEMKFERRI-TLPFFEH--------------------QIAASRNYAFHDIFSL 300
           +   M +    + T+   H                      QI + N+A ++ F
Sbjct: 235 ASVTYMTYGIVVCTIFMLAHVLESTEFLTPDGESGAIDDEWAICQIRTTANFATNNPFWN 294

Query: 301 LIMGGMQYQTEHHFFPQIPFYRLPKARVIIAEELKKWNLKIHEGPIFE 348
           GG+ +Q HH FP I    P+  II +  +++ ++    P F+
Sbjct: 295 WFCGGLNHQVTHHLFPNICHIHYPQLENIIKDVCQEFGVEYKVYPTFK 342
```

Figure 4A

```
M.alpina       1  ------MAAAPSVRTFTRAEVLNAEAINEGKKDAEAPFLMIIDNKVYDVREEVP--DHPGG
C.elegans      1  --------------------------MVIREQE----HEPFFIKIDGKWCQIDAVLR-SHPGG
B.officinalis  1  ------------MAAQIKKYITSDELKNHDK---PGDLMISIQGKAYDVSDWVK--DHPGG
M.musculus     1  MGKGGNQGEGSTERQAPMPTFRWEEIQKHN--LRTDRWLVIDRKVYNVIKMSQ--RHPGG
T.thermophila  1  -------------------------MGVDKTQEEIVLENKPELLNEYKFIYKDTEYDCIEYAKSNKHPGG M.alpina       54 -SVILTHVGK--DGTDVFDTFHPEA----AWETLANFYVGDIDESDRDIKND-----D--
C.elegans      34 -SAITIYKNM--DATTVFHTHTGSKEAYQWLTELKKECPTQEPEIPDIKDDPIKGIDDV
B.officinalis  45 SFPIKSLAGQ-EVIDAFVAFHPAS---TMKNIDKFTGYYLKDYSVSEVS------
M.musculus     57 HRVIGHYSGE--DATDAFRAFHLDLD--FVGKFLKPLLIGELAPEEPSIDRG----
T.thermophila  46 LNFIENLFIDEKQDLTEYERTIHSKQ----ALKILKSFPKTGAKQEH--TESS M.alpina      100 -----FAAEVR----KIRTLFQSEEGYMDSSKAYAYAFKVSFNLCIWGLSTVIVAKW
C.elegans      91 NMGTFNISEKRSAQINKSFTDLRMVRAEGIMDGSPLEVIRKI----LETFIFIFAFY
B.officinalis  91 ------KDYR----KLVFEFSKMGLMD--KKGHIMFAT-LCFIAMLFAMSVYCVL
M.musculus    105 -KSSQITEDFR-----ALKKTAEDVNLFKTNHLFFLLESHIIVMESLAWFLSYE
T.thermophila  92 ------KR-------FSILKKKLKHLFEPNWPIEL------GLFLTIFTLFVT M.alpina      146 GQTSTLANVLSAALLGLFWQQCGWLIAHDFLHHQVFQDRFWGDIFGAFECGVCQ----
C.elegans     146 LQYHTYY-IPSAILNGVAWQQLGWLIHEFAHHQEFKNRYMNDEASYFVGNFLQVSHIFNN
B.officinalis 133 FCEGVLVHLFSGCLMGFLWIQSWIGHDAGHYMVSDSRLNKFMGIFAANCIS------
M.musculus    155 GTGWIPT-LVIAFVIATSQAQAGWLQHDYGHLSVYKKSIWNHVHKFVIGHLK-----
T.thermophila 126 GCLTQKW-YFSIPLIVIEMQIISGWIGHSMNHNRNPILR----KFALVYAPLCG
```

Replacement Sheet
Figure 4B

```
M.alpina         199 GFSSSSWWKDKHNTHHAAPNWHGEDPDNDTHPLLTWSEHALEMFSD--VPDEELTRMWSRF
C.elegans        205 GFSSGGWKEQHNVHHAATNVVGRDGDDLMPFYATVAEHLNNYS----QDS-----WVMT
B.officinalis    186 GISIGWWKWNHNAHHIACNSLEYDPDLQYIPFLVSSKFFGSLISHFYEKRLTFDSLSRF
M.musculus       207 CASANWWNHRHFQHHAKPNILFHKDPDLKSIHVFVLGEWQPLEVG-----KKK----LKYL
T.thermophila    174 GFSNKWWGRKHNQHHMFTNNILKDED------------------I----------------

M.alpina         257 MVLNQITWFYFPIISFARLSWCLQSIIFVLPNGQAHKPSGARVPISLVEQISLAWHNTWYI
C.elegans        256 LFRWQHVHWIFWLPFLRISWLLQSIIFVSQMP-THYYDYYRN-TAIYEQVGLSHHWAWSI
B.officinalis    246 FVSYQHWTFYPIMCAARINMYVQSLIMLLTKR---NVSYRA----QELIGCLVFSIWYP
M.musculus       258 PYNHQHEYFRLIGPELLIPMYFQYQIIWTMIS------RR----DWDIAWAISVYM
T.thermophila    201 -----QHDYKLWQFPELFLKWLLDSIILASYYEF-----------EGIFLALHWVLLF M.alpina         317 ATMFLFLKDPVNM---LVYFIVSQAVCGNILAIVFSINHNGMPVISKEEAVDMDRFTKQII
C.elegans        314 G-QLYFIPDWSTR---IMFLVSHLVGGFILSHVVFHYSVEKFALSSNIMSNYACLQIM
B.officinalis    298 L-LVSCHPNWGER---IMFVIASLSVTG-MQQVQFSLNHFSSSVVGK-PKGNNMFEKQTD
M.musculus       305 RFFYTYIPFYGILGALVFENFIRFHESHWFVWVTQMNHLVWELDLDH---YRDWFSSQLA
T.thermophila    242 N-------QN--FYIMIISELIAGFFSASIIVGNFENEMKFERR--ITLPFFEHQIA M.alpina         375 TGRDVH-PGLFANWTTGGLNYQIEHHLFPSMPRHNFSKIQPAVETLCKKYNVRYHTTGMI
C.elegans        371 TIRNWR-PGRFIDWLWGGLNYQIEHHLFPTMPRHNINTVMPIVKEFAAANGLPYMVDDYF
B.officinalis    353 GTLDIS-CPPWMDWFHGGLQFQIEHHLFPKMPRCNIRKISPYVIELCKKHNLPYNYASFS
M.musculus       362 AICNVE-QSFFNDWESGHLNFQIEHHLFPTMPRHNLHKJAPLVKSLCAKHGIEYQEKPFL
T.thermophila    288 ASRNYAFHDIFSLLIMGGMQYQTEHHLFFQIPFYRLPKARVLAEELKKWNLKIHEGPFF
```

Figure 4C

```
M.alpina       434 ECTAEVFSRLNEVSKAASKMGKAQ---------------- 457
C.elegans      430 TGFWLETEQFRNIANVAAKITKKIA---------------- 454
B.officinalis  412 KANEMTERTLRNTALQARDITKPLPKNLVWEALHTHG     448
M.musculus     421 RALIDIVSSLKKSGELWLDAYLHK---------------- 444
T.thermophila  348 EKSHT----------------------------------- 352
```

Comparison of the fatty acid spectrum (main fatty acids) of the Tetrahymena pBDES6-Transformants (AX601 and AX604) with Tetrahymena wild strain (CU522) after 50 h of cultivation. Value is the percentage of fatty acids relative to total fatty acids.

SEQUENCE LISTING

<160> NUMBER OF SEQ ID NOS: 19

<210> SEQ ID NO 1
<211> LENGTH: 1219
<212> TYPE: DNA
<213> ORGANISM: Tetrahymena thermophila

<400> SEQUENCE: 1

```
agtaagcaaa ctaaatttaa aaaacaagca ttatgggagt tgataagact taagaagaaa      60
ttgttcttga aaataaaccc gaacttctca acgaatacaa atttatttac aaggatactg     120
aatatgactg cactgaatat gctaaatcaa ataagcatcc tggcggtctt aatttcctca     180
atttgtttat tgatgagaag taagatttga ctgaatattt cagaacactc cattctaagt     240
aggctttgaa aattttaaaa tccttcccta agactggcgc aaaataagag gagactgaat     300
cttcaaagag attctcaata ttaaagaaaa agcttaagca tttattcgaa ccaaactggc     360
ctatcgaaat tggtttattc ttaactacct ttactttatt tgtcactgga tgtttgactc     420
aaaagtggta tttctctatt ccccttcttg tcttaatgca aatcatcagt ggttggattg     480
gtcactctat gaaccacaat cgtaaccta tattaagaaa attcgcttta gtctacgctc     540
ctctttgtgg tggtttctct aataaatggt ggggtaggaa gcacaatcaa catcatatgt     600
tcacaaacaa cattctaaag gacgaagata tctaacacga ttacaaattg tggtaattcc     660
ccttcttatt tttaaagtgg aaattagact ccatcttagc ttcttattat gaatttgaag     720
gaatcttcct tgccttgcac tgggtattat tattcaacta aaacttctat atcgtaattc     780
tttctgaatt gattgctggt ttcttcagtg cttctattct tgttggaaat catgaaaatg     840
```

```
aaatgaaatt cgaaagaaga atcactttac cattttttcga acatcaaata gctgcaagca      900
gaaactacgc ttttccacgac atattctctc tacttattat gggtggtatg taatattaga      960
ctgaacatca cttttttccca taaattcctt tctacagatt acccaaagct cgtgtcataa     1020
ttgctgaaga attaaagaag tggaacctta agattcatga aggacctatt tttgaaaaat     1080
ctcacctttg aaaataaata aatttatttt aaatgcatat tttattagta atactaacaa     1140
ttgtaggaaa tgtgttatgg tttgtttact tattactttt taatctgaga aacagtctt      1200
aacaaaaaaa aaaaaaaaa                                                  1219
```

<210> SEQ ID NO 2
<211> LENGTH: 352
<212> TYPE: PRT
<213> ORGANISM: Tetrahymena thermophila

<400> SEQUENCE: 2

```
Met Gly Val Asp Lys Thr Gln Glu Glu Ile Val Leu Glu Asn Lys Pro
1               5                   10                  15

Glu Leu Leu Asn Glu Tyr Lys Phe Ile Tyr Lys Asp Thr Glu Tyr Asp
            20                  25                  30

Cys Thr Glu Tyr Ala Lys Ser Asn Lys His Pro Gly Gly Leu Asn Phe
        35                  40                  45

Leu Asn Leu Phe Ile Asp Glu Lys Gln Asp Leu Thr Glu Tyr Phe Arg
    50                  55                  60

Thr Leu His Ser Lys Gln Ala Leu Lys Ile Leu Lys Ser Phe Pro Lys
65                  70                  75                  80

Thr Gly Ala Lys Gln Glu Glu Thr Glu Ser Ser Lys Arg Phe Ser Ile
                85                  90                  95

Leu Lys Lys Lys Leu Lys His Leu Phe Glu Pro Asn Trp Pro Ile Glu
            100                 105                 110

Ile Gly Leu Phe Leu Thr Thr Phe Thr Leu Phe Val Thr Gly Cys Leu
        115                 120                 125

Thr Gln Lys Trp Tyr Phe Ser Ile Pro Leu Leu Val Leu Met Gln Ile
    130                 135                 140

Ile Ser Gly Trp Ile Gly His Ser Met Asn His Asn Arg Asn Pro Ile
145                 150                 155                 160

Leu Arg Lys Phe Ala Leu Val Tyr Ala Pro Leu Cys Gly Gly Phe Ser
                165                 170                 175

Asn Lys Trp Trp Gly Arg Lys His Asn Gln His Met Phe Thr Asn
            180                 185                 190

Asn Ile Leu Lys Asp Glu Asp Ile Gln His Asp Tyr Lys Leu Trp Gln
        195                 200                 205

Phe Pro Phe Leu Phe Leu Lys Trp Lys Leu Asp Ser Ile Leu Ala Ser
    210                 215                 220

Tyr Tyr Glu Phe Glu Gly Ile Phe Leu Ala Leu His Trp Val Leu Leu
225                 230                 235                 240

Phe Asn Gln Asn Phe Tyr Ile Val Ile Leu Ser Glu Leu Ile Ala Gly
                245                 250                 255

Phe Phe Ser Ala Ser Ile Leu Val Gly Asn His Glu Asn Glu Met Lys
            260                 265                 270

Phe Glu Arg Arg Ile Thr Leu Pro Phe Phe Glu His Gln Ile Ala Ala
        275                 280                 285

Ser Arg Asn Tyr Ala Phe His Asp Ile Phe Ser Leu Leu Ile Met Gly
    290                 295                 300
```

```
Gly Met Gln Tyr Gln Thr Glu His His Phe Phe Pro Gln Ile Pro Phe
305                 310                 315                 320

Tyr Arg Leu Pro Lys Ala Arg Val Ile Ile Ala Glu Glu Leu Lys Lys
                325                 330                 335

Trp Asn Leu Lys Ile His Glu Gly Pro Ile Phe Glu Lys Ser His Leu
                340                 345                 350
```

<210> SEQ ID NO 3
<211> LENGTH: 2492
<212> TYPE: DNA
<213> ORGANISM: Tetrahymena thermophila

<400> SEQUENCE: 3

```
taaaacgatt ataaatatca cacaaattaa accgaaaaag agttaaagtg ctaatattaa      60
taatataatt tatctaaatt gaaagatggt tcaattaatt tgaaattatt ttgaagcaaa     120
ataattcgat tcgtgtaaga tggaaattga aagaattaag gtttagaaaa gttcttttg     180
taaaataata gagttaaagt caataaattt tatattacgt aaatcttaaa gtgtgcaaat    240
gttatcatta acaattctaa atgatgcaaa atatttaaat tattaaaaat aatgatagtt    300
aataaaatca atatttcata ataataataa ggtatctatc tatctatcaa tatttcaata    360
aatattaatt aaaaggttat aaaataagta agcaaactaa atttaaaaaa caagcattat    420
gggagttgat aagacttaag aagaaattgt tcttgaaaat aaacccgaac ttctcaacga    480
atacaaattt atttacaagg atactgaata tgactgcact gaatatgcta atcaaataa    540
gcatcctggc ggtcttaatt tcctcaattt gtttattgat gagaagtaag atttgactga    600
atatttcaga acactccatt ctaagtaggc tttgaaaatt ttaaaatcct tccctaagac    660
tggcgcaaaa taagaggaga ctgaatcttc aaagagattc tcaatattaa agaaaaagct    720
taagcatgta aatacattca aatgatatct ttattgagca tatttagcat aatttgataa    780
ttttcataag catattttaa attataaaaa tgaacatatt tttaaattaa tttagttatt    840
cgaaccaaac tggcctatcg aaattggttt attcttaact accttacttt tatttgtcac    900
tggatgtttg actcaaaagt ggtatttctc tattcccctt cttgtcttaa tgcaaatcat    960
cagtggttgg attggtcact ctatgaacca aatcgtaac cctatattaa gaaaattcgc   1020
tttagtctac gctcctcttt gtggtggttt ctctaataaa tggtggggta ggaagcacaa   1080
tcaagtaacc ataatattta atataaatat ataagatttt tttggttttg cgaggaaaaa   1140
agtcatattt tgatgcttta atagtacaaa caatatttga ttgttatgat taaattatta   1200
aagatcttaa tttagccttt tttaaaaatt tcaaataaat ttgaagataa tattattaaa   1260
gtataataaa tgattaagcc aaaatctgta ccaaaaatct gtaaatacaa aatcaacttc   1320
acacaaagat tacacatagc atttttatttt ttataataaa ataaatgaaa atagtttttt   1380
attttaagaa atgaaataac tttttttccc tatgattttc aattaataaa aagcattgct   1440
atacaaataa ttgaaaaaag ctaaatcttt tttctattaa aattaattac aaattgtaaa   1500
agattaattt taccatttaa tttaagtacc gcaataagca aatctctatt ttttttaagc   1560
aatgacgtca cggataaata ttatcatact attcctcaat aataaatcat ctttaaaata   1620
atttaaaact aattaatata attctaataa agcatcata tgttcacaaa caacattcta   1680
aaggacgaag atatctaaca cgattacaaa ttgtggtaat tccccttctt attttttaaag   1740
tggaaattag actccatctt agcttcttat tatgaatttg aaggaatctt ccttgccttg   1800
cactgggtat tattattcaa ctaaaacttc tatatcgtaa ttctttctga attgattgct   1860
```

-continued

```
ggtttcttca gtgcttctat tcttgttgga aatcatgaaa atgaaatgaa attcgaaaga      1920
agaatcactt taccattttt cgaacatcaa atagctgcaa gcagaaacta cgcttttccac    1980 gacatattct ctctacttat tatgggtggt atgtaatatt agactgaaca tcactttttc     2040
ccataaattc ctttctacag attacccaaa gctcgtgtca taattgctga agaattaaag     2100
aagtggaacc ttaagattca tgaaggacct attttttgaaa aatctcacct ttgaaaataa    2160
ataaatttat tttaaatgca tattttatta gtaatactaa caattgtagg aaatgtgtta     2220
tggtttgttt acttattact ttttaatctg agaaaacagt cttaacattt attcgatttt     2280
atttaacatt acttttaaa aaacaatttt gcttactata aatttacata agtatagtaa      2340
gaaactaagt tgatggtgtt atttttttaat ttttctaatt aatttgtgaa taaacgatga    2400
tttaatttat taatccagca aataggcata attatattac aaataccagc ccgggccgtc     2460
gaccacgcgt gccctatagt gagtcgtatt ac                                   2492
```

<210> SEQ ID NO 4
<211> LENGTH: 10
<212> TYPE: PRT
<213> ORGANISM: Tetrahymena thermophila

<400> SEQUENCE: 4

Trp Trp Lys Trp Asn His Asn Ala His His
1               5                   10

<210> SEQ ID NO 5
<211> LENGTH: 13
<212> TYPE: PRT
<213> ORGANISM: Tetrahymena thermophila

<400> SEQUENCE: 5

Gly Gly Leu Gln Phe Gln Ile Glu His His Leu Phe Pro
1               5                   10

<210> SEQ ID NO 6
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n = a or g or c or t/u

<400> SEQUENCE: 6
tggtggaart ggamncayaa                                                 20

<210> SEQ ID NO 7
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n = a or g or c or t/u

<400> SEQUENCE: 7
cgdggraana rrtgrtgttc                                                 20

<210> SEQ ID NO 8

<211> LENGTH: 40
<212> TYPE: DNA
<213> ORGANISM: Artificial Sequence
<220> FEATURE:
<223> OTHER INFORMATION: Primer

<400> SEQUENCE: 8
gaccacgcgt atcgatgtcg actttttttt ttttttttv            40

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
ggaatcacaa tcaacatcat atgttcac                        28

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
cttcgtcctt tagaatgttg tttgtgaac                       29

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
agtaagcaaa ctaaatttaa aaacaagc                        29

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
agtaagcaaa ctaaatttaa aaacaagc                        29

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
ggtccttcat gaatcttaag gttccacttc                      30

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14

```
cttaagtctt atcaactccc ataatgc                                              27

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
gaagtggaac cttaagattc atgaaggacc                                           30

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
gcattatgca tgttgataag acttaagaag                                           30

<210> SEQ ID NO 17
<211> LENGTH: 35
<212> TYPE: DNA
<213> ORGANISM: Artificial Sequence
<220> FEATURE:
<223> OTHER INFORMATION: Primer

<400> SEQUENCE: 17
tatggatcct caaaggtgag atttttcaaa aatag                                     35

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
aaaaataaaa aagtttgaaa aaaaaccttc                                           30

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gtttagctga ccgattcagt tc                                                   22
```

NUCLEIC ACID WHICH IS OBTAINED FROM *TETRAHYMENA* AND WHICH CODES FOR A DELTA-6-DESATURASE, THE PRODUCTION THEREOF AND USE

This is a U.S. National Phase Application Under 35 U.S.C. § 371 and Applicants herewith claim the benefit of priority of PCT/EP00/08778 filed Sep. 8, 2000, which was published Under PCT Article 21(2) in German and Application No. 199 43 270.8 filed in Germany on Sep. 10, 1999.

The present invention relates to a *Tetrahymena* delta-6-desaturase, to its encoding nucleic acid and to its preparation and use.

The invention relates to a *Tetrahymena* nucleic acid which encodes a ciliate-specific delta-6-desaturase which is involved in the biosynthesis of commercially valuable polyunsaturated fatty acids (what are termed PUFAs, i.e. polyunsaturated fatty acids) in eukaryotes. In this connection, the nucleic acids according to the invention, and the polypeptides which can be obtained from them, exhibit surprisingly little sequence identity with other known natural desaturases. The invention furthermore relates to the use of the nucleic acids for overexpression in eukaryotes, in particular ciliates, preferably *Tetrahymena*, particularly preferably *Tetrahymena thermophila*, with the aim of specifically modifying the fatty acid spectrum, in particular with the aim of increasing PUFA formation.

The nucleic acids according to the invention can be obtained from ciliates, preferably from *Tetrahymena*, particularly preferably from *Tetrahymena thermophila*, a GLA-producing organism having a very high content of GLA.

FIG. 1 shows a general scheme of the biosynthesis of PUFAs, and the enzymes involved, in eukaryotes (modified after Gill & Valivety, Trends Biotechnol. 1997, 15:401–409). The conversion of stearic acid (18:0) to oleic acid (18:1 Δ9) is catalyzed by a delta-9-desaturase. Oleic acid is converted by a delta-12-desaturase into linoleic acid (18:2 Δ9,12; abbreviated to LA), which is in turn converted by a delta-6-desaturase into γ-linolenic acid (18:3, Δ6,9,12; abbreviated to GLA) or by a delta-15-desaturase into α-linolenic acid (18:3 Δ9,12,15; abbreviated to ALA). The fatty acids are extended by elongases, as a result of which dihomo-γ-linolenic acid (20:3 Δ8,11,15; abbreviated to DGLA) is, for example, formed from γ-linolenic acid, with the dihomo-γ-linolenic acid in turn being converted by a delta-5-desaturase into arachidonic acid (20:4 Δ5,8,11,15; abbreviated to ARA), which is a direct precursor of physiologically active eicosanoids, such as prostaglandins, prostacyclins, thromboxanes and leukotrienes. The conversion of LA to GLA by delta-6-desaturase has been found to be a limiting step in the formation of the PUFAs (termed delta-6-unsaturated fatty acids in that which follows) which are derived from GLA (Huang Y S & Mills D E (1996) γ-Linolenic acid. Metabolism and its role in nutrition and medicine. AOCS Press, Champaign, Ill., 1996).

While an enzyme having delta-6-desaturase activity is known to be present in *Tetrahymena setosa* and *T. pyriformis* (Peng, Y. M. and Elson, C. E. (1971) J. Nutr. 101, 1177–1184), a homogeneous protein which is derived from a ciliate and which possesses such an activity has not previously been made available (e.g. Koll, M. and Erwin, J. A. (1990) J. Protozool. 37(3), 229–237).

Since vertebrates are unable to insert any double bonds behind position 9 in fatty acids, unsaturated fatty acids such as LA and ALA are essential nutrients which vertebrates cannot synthesize (see FIG. 1) and, in the diet, are principally derived from plant sources. In mammals, a delta-6-desaturase can convert LA into GLA, which is a precursor of ARA, which is in turn an essential precursor of most prostaglandins. The formation of stearidonic acid (18:4 Δ6,9,12,15), which is a precursor of EPA, from ALA is likewise catalyzed by means of delta-6-desaturase. Delta-6-desaturase is consequently the first essential step in the biosynthesis of the eicosanoids (see FIG. 1).

It has been found that, in mammals, the activity of delta-6-desaturase can be impaired by factors such as alcohol consumption, stress, deficient nutrition and aging processes (Huang & Mills, 1996; Horrobin (1990) Rev. Contemp. Pharmacother. 1:1–45; Bolton-Smith C et al. (1997) Eur. J. Clin. Nutr. 51:619–624; Leventhal L J et al. (1993) Ann. Intern. Med. 119:867–873). This leads to an insufficient supply of GLA and thus ultimately a deficiency in the molecules derived from GLA, such as ARA and the physiologically important eicosanoids which are formed therefrom, since, as has already been mentioned, the formation of GLA from LA by delta-6-desaturase is a limiting step in PUFA synthesis (Brenner R R (1976) Adv. Exp. Med. Biol. 83:85–101; Nakahara T et al. (1993) J. Jpn. Oil Chem. Soc. 42:242–253; Chapkin, R S (1998) Reappraisal of the essential fatty acids. In: Fatty acids in food and their health implications, 2$^{nd}$ ed. (Chow C K, ed) Marcel Dekker, New York, N.Y.). Supplying GLA can both compensate for a reduced endogenous level of delta-6-unsaturated fatty acids and cover an increased requirement for these fatty acids (Horrobin (1990)). The uptake of GLA via the diet is therefore advantageous for the biosynthesis of GLA-derived molecules (Fan, Y Y & Chapkin, R S (1998) J. Nutr. 128:1411–1414).

The finding that GLA exerts many different positive influences on the human body has by now been underpinned by a large number of scientific studies. Thus, clinical studies have demonstrated the positive effect of CLA on, for example, atopic eczema (Shinaski, H: PUFA content and effect of dietary intake of γ-linolenic acid-rich oil on profiles of n-6, n-3 metabolites in plasma of children with atopic eczema. J. Clin. Biochem. Nutr. (1995), 19(3), 183–192), rheumatoid arthritis (Zurier T B, Rossetti R G, Jacobson E W, DeMarco D M, Liu N Y, Temming J E, White B M, Laposata M (1996) γ-Linolenic acid treatment of rheumatoid arthritis: A randomized, placebo-controlled trial. Arthritis Rheum. 39(11) 1808–1817), atherosclerosis (Leng G C, Lee A J, Fowkes F G R, Jepson R G, Lowe G D O, Skinner E R, Mowat B F, Randomized controlled trial of γ-linolenic acid and eicosapentaenoic acid in peripheral arterial disease. Clinical Nutrition, (1998) 17/6 265–271), diabetic neuropathy (Pfeifer M A, Schumer M P (1995) Clinical trials of diabetic neuropathy: past, present, and future. Diabetis 44(12) 1355–61), migraine (Wagner W, Nootbaar-Wagner U (1997) Prophylactic treatment of migraine with γ-liolenic and alpha-linolenic acids, Cephalalgia 17/2 127–130), schizophrenia (Vaddadi, K S. (1982) Some observations on the use of prostaglandin E1 precursor in the treatment of schizophrenia. Biol. Aspects Schizophr. Addict. 183–91. Publisher: Wiley, Chichester, U K) and cancer (Kairemo KJA, Jekunen A P, Korppi-Tommola E T, Pyrhonen S O (1997) Effects of lithium γ-linolenate on the perfusion of liver and pancreatic tissues in pancreatic cancer. Anticancer Research 17/5 B 3729–3736). These studies achieved both a statistical improvement and a clinically significant improvement in the clinical picture. The effect of GLA in this connection is due, in particular, to the formation of eicosanoids (prostaglandins, prostacyclins, thromboxanes and leukotrienes), for whose biosynthesis GLA is a precursor molecule (FIG. 1).

Because of these positive properties, a broad spectrum of application exists for GLA in the pharmaceutical industry, the cosmetics industry, the animal feed industry and the foodstuffs industry (Horrobin (1990), Horrobin (1992) Prog. Lipid Res. 31:163–194; Chapkin (1998), Fan & Chapkin (1998)).

Most PUFAs found in humans and animals are either derived directly from the diet or formed by the conversion, by desaturases and elongases, of the essential fatty acids which are supplied via the diet. For this reason, the PUFA biosynthesis genes which are derived from organisms in which these PUFAs occur naturally are of great commercial interest. The commercial production of PUFAs can be achieved in organisms or cells by expressing these genes in the systems in a specific and functional manner. For this reason, a requirement exists for genes encoding desaturases and elongases involved in PUFA biosynthesis and for using these genes for obtaining PUFAs and PUFA oils commercially by means of reliable and economic methods.

None of the commercially employed oilseeds produces GLA. On the contrary, GLA only occurs in the oil derived from seeds of various plants such as common evening primrose (*Oenothera biennis*, approx. 10% GLA), borage (*Borago officinalis*, approx. 23%) and blackcurrant (*Ribes nigrum*, approx. 18%). In addition to this, a variety of microorganisms, such as the fungi *Mucor* and *Mortierella* (up to approx. 25%), the blue-green alga *Spirulina* (approx. 12–18%), and others, are known to be sources of GLA. Ciliates such as *Tetrahymena* (up to 47%; Hill, D L (1972) The biochemistry and physiology of Tetrahymena. Chapter 3, 46–73. Academic press, New York, London; Erwin, J & Bloch, K (1963) J. Biol. Chem. 238:1618–1624) have been reported to be a particularly rich source of GLA. Phillips & Huang provide a good review of the natural sources of GLA (Phillips J C, Huang Y S (1996) Natural sources and biosynthesis of γ-linolenic acid: an overview. 1–13 in: γ-linolenic acid. Metabolism and its role in nutrition and medicine, Huang Y S, Mills D E (eds.) AOCS Press, Champaign, Ill., 1996).

However, the commercial isolation of GLA from these natural sources is associated with a number of disadvantages. Both the quality and the quantity of the oils obtained from these organisms vary and, in some cases, the composition of the oils is very heterogeneous, making it necessary to use elaborate and expensive purification steps for the purpose of concentrating the GLA. In addition to this, cultivating GLA-containing plants is not a very economical process (Hansen C E et al. (1991) J. Sci. Food Agric. 54:309–312). It has been found that the space/time yield for obtaining GLA-containing oil is markedly better in some CLA producing microoraganisms than in higher plants. For this reason, the fermentative preparation of GLA using microorganisms offers a promising alternative to other sources of GLA. The fatty acid spectrum of many microorganisms is frequently rather simple as compared with that of higher organisms, a feature which offers great advantages during purification. Furthermore, fermentative preparation is not dependent on external factors such as weather, supply of nutrients, etc. In addition, PUFAs which are prepared in this way are to a large extent free of contaminants which can be attributed, for example, to environmental pollution. A further advantage is that, in contrast to GLA derived from natural sources, GLA which is isolated by fermentative processes is not subject to any fluctuations in availability.

There have already been attempts to develop systems for isolating GLA by fermentation (Ratledge C (1993) Trends Biochem. 11:278–284; Ratledge C (1989) Biochem. Soc. Trans. 17:1139–1141; Gosselin Y et al. (1989) Biotechnol. Lett. 11:423–426; WO86/03518). However, when microorganisms are to be used for commercially producing GLA by fermentation, it is desirable to increase the content of GLA since the fermentation of PUFA-producing microorganisms is regarded as being relatively elaborate and expensive and consequently not very economical (see Ratledge 1993 above). Because of its relatively high content of GLA (see above), *Tetrahymena thermophila* is particularly suitable for obtaining GLA by fermentation. *Tetrahymena* can be readily cultured in a fermenter and high cell densities can be achieved (Kiy, T. & Tiedtke (1992) Appl. Microbiol. Biotechnol. 37, 576–579; Kiy, T. & Tiedtke, A. (1992) Appl. Microbiol. Biotechnol. 38, 141–146).

The object of the present invention is therefore to provide *Tetrahymena* nucleic acids which encode a polypeptide having the activity of delta-6-desaturase and which are functionally expressed and overexpressed in a host organism, preferably in *Tetrahymena*, for the purpose of accumulating GLA and/or delta-6-unsaturated fatty acids.

The present invention therefore relates to a nucleic acid which is depicted in SEQ ID No.: 1 and which encodes a delta-6-desaturase having an amino acid sequence as depicted in SEQ ID No.: 2, or a functional variant thereof, and parts thereof containing at least 8 nucleotides, preferably containing at least 15 or 20 nucleotides, in particular containing at least 100 nucleotides, especially containing at least 300 nucleotides (termed "nucleic acid(s) according to the invention" in that which follows). The invention furthermore likewise relates to a nucleic acid which is depicted in SEQ ID No.: 3, which contains the genomic sequence and which, in addition to the sequence encoding a delta-6-desaturase, also contains noncoding nucleic acid sequences such as introns, promoter and flanking sequences.

The complete nucleic acid depicted in SEQ ID No.: 1 encodes a protein which contains 352 amino acids and which has a theoretical molecular mass of 41.8 kDa. The sequence analyses according to the present invention confirm that the nucleic acid is a nucleic acid which encodes a *Tetrahymena* delta-6-desaturase.

A homology comparison was used to identify the protein sequence which is derived from the nucleic acid sequence (SEQ ID No.: 1), and which is depicted in SEQ ID No.: 2. as being a delta-6-desaturase. The BLASTP function (Altschul et al. (1997) Nucleic Acids Res. 25:3389–3402) was used for the homology comparison. Desaturases, in particular delta-6-desaturases (E. C. 1.14.99.25; linoleoyl-CoA desaturase) were identified from the databases as being homologous proteins (see FIG. 2). In this connection, the known delta-6-desaturases exhibit a maximum identity of 25% with the polypeptide sequence according to the invention (see FIGS. 3A–3E). A multiple alignment of various known delta-6-desaturases with the polypeptide sequence according to the invention is shown in FIG. 4. The homologies are to be found, in particular, in conserved domains such as the histidine boxes (Los & Murata, 1998. Biochem. Biphys. Acta 1394: 3–15; Shanklin, J et al. 1997. Proc. Natl. Acad. Sci. USA 92, 6743–6747). In addition to this, it was possible to identify a cytochrome b5 domain as in other eukaryotic delta-6-desaturases (Lederer, F. (1994) Biochimie 76, 674–692; Cho et al. J. Biol. Chem. 1999, 274(1): 471–477). Although the polypeptide sequence according to the invention can be identified as being a delta-6-desaturase, it differs substantially from other delta-6-desaturases. It is particularly striking that, with 352 amino acids, the sequence is around 20% shorter than other eukaryotic delta-6-desaturases. In addition to this, the sequence exhibits a large number of unique differences in strongly conserved regions. Thus, the HHLFP motif, which is 100% conserved in other delta-6-desaturases, has been changed into HHFFP (see FIG. 4). For these reasons, the degree of identity of the polypeptide sequence according to the invention with known desaturases is surprisingly low.

The fatty acid spectrum can be significantly modified by specifically overexpressing the desaturase in *Tetrahymena*, for example (see Tables 1 and 2). Under these circumstances, the ratio of saturated and unsaturated fatty acids is displaced in the direction of significantly more unsaturated fatty acids. Of particular interest in this connection is the increase in the productivity of GLA which can be achieved in this way.

In a preferred embodiment, the nucleic acid according to the invention is a DNA or RNA, preferably a double-stranded DNA, and in particular a DNA having a nucleic acid sequence, or a functional variant of the nucleic acid sequence, as depicted in SEQ ID No.: 1 from pos. 33 to pos. 1091. In accordance with the present invention, the two positions determine the start and the end of the coding region.

According to the present invention, the term "functional variant" is understood as meaning a nucleic acid which is related functionally to the *Tetrahymena* delta-6-desaturase. Examples of related nucleic acids are, for example, nucleic acids from other ciliate cells, or allelic or degenerate variants. The invention likewise encompasses functional variants of the nucleic acids according to the invention which, because of the unusual codon usage (see: Wuitschick J D, Karrer K M (1999) Analysis of genomic G+C content, codon usage, initiator condon context and translation termination sites in *Tetrahymena thermophila*. J. Eukaryot. Microbiol. 1999 46(3):239–47), require an adaptation of the nucleic acids according to the invention in selected expression systems. On the one hand, this relates to the replacement of the codons TAA and TAG, which encode glutamine in ciliates and which are stop codons in most other expression systems, with CAA and CAG. In addition to this, the skilled person is familiar with optimally adapting the nucleic acids according to the invention to the given particular codon preference (what is termed codon usage) of different expression systems. The nucleic acids can be modified in a known manner by specifically substituting bases or else the nucleic acid which is required is obtained from artificially prepared oligonucleotides. The adaptation of the sequence can be carried out, for example, on the basis of the known codon usage tables (e.g. on the Internet: Codon usage tabulated from Genbank) for the preferred expression systems. The present invention also encompasses variants of nucleic acids which only contain parts of the nucleic acid.

According to the present invention, the term "variants" is understood, in a broader sense, as meaning nucleic acids which exhibit a homology, in particular a sequence identity, of approx. 60%, preferably of approx. 75%, in particular of approx. 90% and especially of approx. 95%.

The parts or fragments of the nucleic acids according to the invention can, for example, be used for preparing individual epitopes, as probes for identifying other functional variants, or as antisense nucleic acids. For example, a nucleic acid comprising at least approx. 8 nucleotides is suitable for use as an antisense nucleic acid, while a nucleic acid comprising at least approx. 15 nucleotides is suitable for use as a primer in the PCR method, a nucleic acid comprising at least approx. 20 nucleotides is suitable for identifying other variants, and a nucleic acid comprising at least approx. 100 nucleotides is suitable for use as a probe.

In another preferred embodiment, the nucleic acid according to the invention contains one or more noncoding sequences (UTR inter alia). The noncoding sequences are, for example, intron sequences or regulatory sequences, such as promoter or enhancer sequences, for the controlled expression of the delta-6-desaturase-encoding gene. The invention therefore relates to a nucleic acid according to the invention as depicted in SEQ ID No.: 3, which nucleic acid can be isolated from *Tetrahymena thermophila* and represents the genomic sequence of the delta-6-desaturase together with introns, promoter and UTRs.

In a further embodiment, the nucleic acid according to the invention is therefore contained in a vector, preferably in an expression vector.

The expression vectors can, for example, be prokaryotic or eukaryotic expression vectors. An example of a prokaryotic expression vector for expression in *E. coli* is the T7 expression vector pGM10 (Martin, 1996), which encodes an N-terminal Met-Ala-His6 tag, which enables the expressed protein to be advantageously purified by way of an Ni2+-NTA column. Examples of eukaryotic expression vectors which are suitable for expression in *Saccharomyces cerevisiae* are the vectors p426Met25 or p426GAL1 (Mumberg et al. (1994) Nucl. Acids Res., 22, 5767) while examples of such vectors which are suitable for expression in insect cells are baculovirus vectors, as disclosed in EP-B1-0127839 or EP-B1-0549721, and for expression in mammalian cells SV40 vectors, which are available generally.

In general, the expression vectors also contain regulatory sequences which are suitable for the host cell, such as the trp promoter for expression in *E. coli* (see, for example, EP-B1-0154133), the ADH-2 promoter for expression in yeast (Russel et al. (1983), J. Biol. Chem. 258, 2674), the baculovirus polyhedrin promoter for expression in insect cells (see, for example, EP-B1-0127839) and the early SV40 promoter or LTR promoters derived, for example, from MMTV (mouse mammary tumor virus; Lee et al. (1981) Nature, 214,228).

The vectors described, for example, by Gaertig et al. ((1999) Nature Biotech. 17: 462–465) or Gaertig & Kapler ((1999) Methods in Cell Biol. 62:485–500) are suitable for the transformation of, and expression in, *Tetrahymena*.

The nucleic acids according to the invention can be synthesized, for example chemically, for example in accordance with the phosphotriester method, using the sequences disclosed in SEQ ID No.: 1 and 3 or using the peptide sequence disclosed in SEQ ID No.: 2 and enlisting the genetic code (see, for example, Uhlman, E. & Peyman, A. (1990) Chemical Reviews, 90, 543, No. 4). Another possibility of obtaining the nucleic acids according to the invention is to use a suitable probe to isolate them from a suitable gene library which has been prepared from an organism which possesses delta-6-desaturase activity (see, for example, Sambrook, J. et al. (1989) Molecular Cloning. A laboratory manual. 2nd edition, Cold Spring Harbor, N.Y.). Examples of suitable probes are single-stranded DNA fragments having a length of from approx. 100 to 1000 nucleotides, preferably having a length of from approx. 200 to 500 nucleotides, in particular having a length of from approx. 300 to 400 nucleotides, whose sequence can be derived from the nucleic acid sequence depicted in SEQ ID No. 1 or 3.

For this reason, the invention likewise relates to a process for preparing a nucleic acid according to the invention, with the nucleic acid being synthesized chemically or being isolated from a gene library using a probe.

The present invention furthermore also relates to the polypeptide itself having an amino acid sequence as depicted in SEQ ID No.: 2, or a functional variant thereof and parts thereof containing at least six amino acids, preferably containing at least 12 amino acids, in particular containing at least 65 amino acids and especially containing at least 150 amino acids (termed "polypeptide according to the invention" in that which follows). For example, a polypeptide of approx. 6–12 amino acids in length, preferably of approx. 8 amino acids in length, can contain an epitope which, after having been coupled to a carrier, can be used for preparing specific polyclonal or monoclonal antibodies (in this regard, see, for example, U.S. Pat. No. 5,656,435). Polypeptides having a length of at least approx. 65 amino acids can also be used directly, without any carrier, for preparing polyclonal or monoclonal antibodies.

Within the meaning of the present invention, the term "functional variant" is understood as meaning polypeptides which are related functionally to the peptide according to the invention, i.e. exhibit a delta-6-desaturase activity.

In a broader sense, it is also understood as meaning polypeptides which possess a sequence homology, in particular a sequence identity, of approx. 70%, preferably of approx. 80%, in particular of approx. 90%, especially of approx. 95%, with the polypeptide having the amino acid sequence as depicted in SEQ ID No.: 2.

Preference is furthermore given to polypeptides which possess conserved regions of histidine boxes and a cytochrome b5 domain. Particular preference is given to polypeptides according to the invention which contain an HHFFP motif.

The term "functional variant" furthermore also includes deletions of the polypeptide in the range of approx. 1–60, preferably of approx. 1–30, in particular of approx. 1–15, especially of approx. 1–5, amino acids. For example, the first amino acid methionine can be missing without the function of the polypeptide being significantly altered. The term "functional variant" also includes fusion proteins which contain the above-described polypeptides according to the invention, with the fusion proteins themselves already possessing the function of a delta-6-desaturase or only being able to gain the specific function after the fusion moiety has been eliminated. These fusion proteins especially include fusion proteins containing a constituent moiety of, in particular, non-ciliate sequences of approx. 1–200, preferably approx. 1–150, in particular approx. 1–100, especially approx. 1–50, amino acids. Examples of non-ciliate peptide sequences are prokaryotic peptide sequences, derived, for example, from *E. coli* galactosidase, or what is termed a histidine tag, for example a Met-Ala-His6 tag. A fusion protein containing what is termed a histidine tag is particularly advantageously suitable for purifying the expressed protein by way of metal ion-containing columns, for example by way of an Ni2+-NTA column. "NTA" stands for the chelator nitrilotriacetic acid (Qiagen GmbH, Hilden).

The parts of the polypeptide according to the invention represent epitopes, for example, which epitopes can be specifically recognized by antibodies.

The polypeptide according to the invention can, for example, be prepared, in accordance with methods which are well known to the skilled person, by expressing the nucleic acid according to the invention in a suitable expression system as already described above. Examples of suitable host cells are the *E. coli* strains DH5, HB101 or BL21, the yeast strain *Saccharomyces cerevisiae*, the insect cell line Lepidopteran, for example obtained from *Spodoptera frugiperda*, or animal cells such as COS, Vero, 293 and HeLa, all of which are available generally.

In particular, said parts of the polypeptide can also be synthesized with the aid of classical peptide synthesis (Merrifield technique). They are suitable, in particular, for obtaining antisera which can be used for screening suitable gene expression libraries in order, in this way, to obtain further functional variants of the polypeptide according to the invention.

The present invention therefore also relates to a process for preparing a polypeptide according to the invention, with a nucleic acid according to the invention being expressed in a suitable host cell and, where appropriate, isolated.

The present invention also relates to antibodies which react specifically with the polypeptide according to the invention, with either the abovementioned parts of the polypeptide themselves being immunogenic, or it being possible for these parts to be made immunogenic, or for their immunogenicity to be increased, by coupling them to suitable carriers, such as bovine serum albumin.

The antibodies are either polyclonal or monoclonal. The preparation, to which the present invention likewise relates, is effected, for example, in accordance with well-known methods by immunizing a mammal, for example a rabbit, with the polypeptide according to the invention, or said parts thereof, where appropriate in the presence of, for example, Freund's adjuvant and/or aluminum hydroxide gels (see, for example, Diamond, B. A. et al. (1981) The New England Journal of Medicine, 1344). Well-known methods can subsequently be used to readily isolate the polyclonal antibodies, which have been formed in the animal as a result of an immunological reaction, from the blood and purify them, for example by means of column chromatography. Preference is given to an affinity purification of the antibodies, in which the C-terminal desaturase fragment has, for example, been coupled to an NHS-activated HiTrap column.

Monoclonal antibodies can be prepared, for example, in accordance with the known method of Winter & Milstein (Winter, G. & Milstein, C. (1991) Nature, 349, 293).

Although delta-6-desaturases have already been described in other organisms, *Tetrahymena* is suitable, because of the particularly high space/time yield when producing GLA, for use both as a starting point for generating highly productive, commercially important strains by means of recombinant methods and as a source of genes for PUFA biosynthesis. Accordingly, the delta-6-desaturase which is derived from the GLA-producing ciliate *Tetrahymena thermophila* and its use are described in the present invention.

The use of recombinant methods to specifically modify the composition of the fatty acid spectrum is described in Napier J et al. (Curr. Opin. Plant Biol. (1999) 123–127), Murphy & Piffanelli (Soc. Exp. Biol. Semin. Ser. 67 (Plant Lipid Biosynthesis), (1998) 95–130) and Facciotti & Kiauf (in: Adv. Photosynth. 6: Lipids in Photosynthesis: Structure, Function and Genetics. Siegenthaler & Murata (eds.) Kluwer Academic Publishers, Netherlands. (1998) 225–248).

The documents WO98/46763, WO98/46764 and WO98/46765 describe desaturases derived from the fungus *Mortierella* and the use of the genes for producing PUFAs, and also some partial sequences of desaturases WO93/06712 and WO96/21022 describe Δ6-desaturases derived from a cyanobacterium and from borage and also the use of these sequences for producing PUFAs in cyanobacteria and plants. WO99/27111 describes a desaturase derived from nematodes and its use for producing PUFAs. Delta-6-desaturases are also disclosed in the literature. These delta-6-desaturases are, however, in particular, delta-6-desaturases from plants (borage (Sayanova et al. (1997) Proc. Natl. Acad. Sci. USA 1997, 94:4211–4216), *physcomitrella* (Girke et al. (1998)

Plant-J. 1998 15(1): 39–48), sunflower (Sperling et al. (1995) Eur. J. Biochem. 1995, 232: 798–805)), fungi (*mortierella*), animals (mouse, rat, *caenorhabditis* (Napier et al. (1998) Biochem. J. 330(2), 611–614)), and cyanobacterium (Reddy et al. (1993) Plant Mol. Biol. 1993, 293–300).

In general, the aim is the functional, heterologous expression of these genes in crop plants, in particular oilseeds such as colza, sunflower and others. However, in all the cases which have so far been published, the GLA yields are either very low and/or the GLa-producing organisms which possess delta-6-desaturase activity and which have been generated by genetic engineering are without commercial importance (Knutzon & Knauf (1998) Soc. Exp. Biol. Semin. Ser. 67:287–304).

Murphy (Current Opinion in Biotechnology (1999) 10:175–180) and Knutzon & Knauf (1998), for example, describe the problems and difficulties involved in specifically modifying the fatty acid spectrum in transgenic plants.

Because of the described high content of GLA in *Tetrahymena*, it is advantageous to use the PUFA biosynthesis genes from this organism for developing highly productive, commercially important strains by means of recombinant methods. As a result of the possibility of being able to cultivate *Tetrahymena* well in mass culture and with a high cell density, it is additionally advantageous to use *Tetrahymena* itself for generating such highly productive, commercially interesting strains by means of recombinant methods. Furthermore, with the aid of the nucleic acid according to the invention, it is also possible to use other organisms, besides *Tetrahymena*, for producing GLA and other delta-6-unsaturated fatty acids.

The preparation of GLA by fermenting *Tetrahymena* is particularly advantageous on account of the rather simple fatty acid spectrum as compared with higher organisms. In addition to this, a fermentative production is not affected by external factors such as weather, supply of nutrients, etc. In addition, a product which is obtained in this way is to a large extent free of impurities which can be generated, for example in the case of products obtained from nature, by environmental pollution.

It is possible to use the nucleic acids according to the invention, encoding a ciliate-specific *Tetrahymena* delta-6-desaturase, to generate transgenic organisms which produce GLA and delta-6-unsaturated fatty acids or whose content of such fatty acids is sibstantially increased as compared with wild-type cells (in this case: *Tetrahymena thermophila*) (see Tables 1 and 2). These transgenic organisms are preferably ciliates, particularly preferably *Tetrahymena*, which harbor the nucleic acid sequence according to the invention or express it in a functional manner. The expression of the desaturase in this way leads to a relative increase in delta-6-unsaturated fatty acids, or of secondary products derived therefrom, with this increase being based on a change in the concentration of enzymes and substrates involved in PUFA synthesis. The invention can be used in the commercial production of PUFAs, in particular of GLA and PUFAs which are derived therefrom, or other secondary products which can be derived from GLA, or of Δ6-unsaturated fatty acids (see FIG. 1: PUFA biosynthesis). In addition to GLA, it is also possible, in this way, by desaturating ALA, to prepare stearidonic acid (18:4 Δ6,9,12,15), for example, which is a raw material which is frequently employed industrially.

In a special embodiment, it is possible, by using the delta-6-desaturase-encoding nucleic acids according to the invention in functional combination with suitable regulatory sequences, to effect an increased expression of the enzyme and thereby to increase the GLA content in GLA-producing organisms or to produce GLA in LA-producing organisms. Oil-producing organisms, such as sunflower, colza and soybean, and also other organisms as well, are of particular interest in this connection. In addition to this, by simultaneously using, for example, a delta-12-desaturase (e.g. Sakuradani E et al. (1999) Eur. J. Biochem. 261:812–820, Okuley et al. Plant Cell (1994) 6(1) 147–58), it is possible to produce said PUFAs in organisms or cells which contain no LA or only a little LA. It is likewise possible to use a combination of the three desaturases which are involved in the formation of GLA, i.e. Δ6, Δ9 and Δ12, for producing GLA and delta-6-unsaturated fatty acids. Furthermore, combining with other genes involved in PUFA biosynthesis (cf. FIG. 1) constitutes another preferred embodiment of the invention, with the GLA and delta-6-unsaturated fatty acids being transformed by means of other enzymes for which GLA serves as a substrate, as a result of which it is possible to prepare, for example, ARA (20:4) and other molecules which are derived from GLA.

In addition, the invention can be used for preparing novel GLA-containing nutrient sources or nutrient sources which are rich in molecules (in particular PUFAs, e.g. ARA) which can be derived from GLA or other Δ6-unsaturated fatty acids.

In addition, the present invention describes expression constructs which contain the delta-6-desaturase gene, or parts thereof, and also the functional combination of the delta-6-desaturase-encoding sequence with heterologous regulatory sequences.

The invention furthermore relates to the preparation of transgenic organisms having an elevated content of GLA (see Tables 1 and 2) by means of using the described delta-6-desaturase-encoding DNA sequence and the described functional constructs of the delta-6-desaturase gene.

A large number of well-established methods are known for isolating genomic DNA and mRNA and for preparing genomic libraries and cDNA libraries (e.g. in Sambrook et al. (1989) in Molecular Cloning: A Laboratory Manual, Cold Spring Harbor, N.Y.). Suitable vectors which contain the desaturase described in the invention, or parts thereof, can be prepared using methods which are known to the skilled person, as are described, for example, in Ausubel et al. (Ausubel et al. (1995), Current Protocols in Molecular Biology, Green Publishing Associates, New York) and Sambrook et al. (1989).

Vectors which contain the delta-6-desaturase-encoding sequence can be introduced into cells by infection, transfection, electroporation, bombardment with particles and other methods. In the present instance, transformation is understood generally as meaning the introduction of foreign DNA into a cell. The methods for doing this are well established and can be carried out in a manner known to the skilled person (e.g. Sambrook et al. (1989), Potrykus I (1991) Annu. Rev. Plant Biol. Plant Mol. Biol. 42:205–225, Christou P (1993) Curr. Opp. Biotech. 4:135–141).

Vectors are also described, with these vectors containing the DNA sequence of the present invention, or parts of the sequence, in functional combination with promoters, or other regulatory elements, which are active in a host cell. In a preferred embodiment, these regulatory elements are nucleic acid sequences which are functionally active in ciliates, in particular *Tetrahymena*, such as the promoters for histone H4, and α- and β-tubulin and others.

Organisms which express the described delta-6-desaturase-encoding sequence recombinantly are also described in the present invention. As a result, in addition to the possibility of producing Δ6-PUFAs in these organisms, there is also the possibility, for example, of isolating the recombinant delta-6-desaturase, or parts thereof, using standard methods of protein purification (e.g. Ausubel et al. (1995)). Vectors which can be used for expressing the delta-6-desaturase-encoding sequence in various organisms can be prepared in a manner known to the skilled person. Detailed information concerning suitable vectors can be found, for example, in Sambrook et al. (1989), Goeddel, ed. (1990) Methods in Enzymology 185 Academic Press, and Perbal (1988) A Practical Guide to Molecular Cloning, John Wiley and Sons, Inc. These vectors preferably contain sequence elements which influence expression, such as promoters, enhancer elements, upstream activating sequences, etc. Inducible and constitutive promoters, or, for example, tissue-specific promoters, are suitable for effecting expression. The cauliflower mosaic virus (CaMV) 35S promoter (Restrepo et al. (1990) Plant Cell 2 987), for example, or, for example, promoters which are activated in association with seed development, are suitable for expression in plant cells.

The vectors which are employed are preferably shuttle vectors (Wolk et al. (1984) Proc. Natl. Acad. Sci. USA, 1561–1565, Bustos et al. (1991) J. Bacteriol. 174: 7525–7533).

In a preferred embodiment, the nucleic acid according to the invention is expressed in *Tetrahymena* under the control of a strong promoter (such as the *Tetrahymena* β-tubulin promoter, Gaertig et al. (1999) Nature Biotech.). The transformation can preferably be effected in accordance with methods described by Gaertig et al. (1999) Nature Biotech. 17:462–465 (or, for example, by Gaertig & Gorovsky (1992) Proc. Natl. Acad. Sci. USA 89:9196–9200). It is possible, for example, to use the *Tetrahymena thermophila* α- or β-tubulin promoters as regulatory elements for the expression. The transformed *Tetrahymena* cells are identified in selective media and then enriched and cultured. It is possible to use standard methods to isolate the lip(o)ids from the cells (e.g. Dahmer et al., (1989) Journal of American Oil Chemical Society 66, 543). The methyl esters of the fatty acids can be analyzed by gas chromatography.

The isolated nucleic acids, or parts thereof, which are described in the present invention can also be used for isolating related genes from other organisms, in particular, for example, from other protists, in particular ciliates. The nucleic acid according to the invention, or parts thereof, can be employed as a labeled probe for isolating homologous genes. Homologous nucleic acid sequences can be identified and isolated by hybridizing the probe to nucleic acids which have been isolated from other organisms. The probe can be labeled in a manner known to the skilled person (Ausubel, Sambrook (see above)). Radioactive nucleotides, or nucleotides which are linked to detectable molecules such as fluorescent molecules, digoxigenin, biotin, magnetic molecules or enzymes, are suitable, for example, for labeling the probe. Homologous DNA sequences are identified and isolated by detecting the label after having hybridized the probe to heterologous DNA. cDNA libraries or genomic libraries are suitable for searching for homologous sequences. In addition to this, Southern and Northern blots are suitable for detecting homologous sequences. Alternatively, it is also possible to isolate homologous DNA which hybridizes with the labeled probe by selective retention of the labeled probe (for example using a magnet).

The use of crosshybridization to isolate and clone homologous genes can be effected by means of methods which are known to the skilled person and which are described, for example, in Ausubel et al. (1995, Current Protocols in Molecular Biology, Green Publishing Associates, New York) or Sambrook et al. (1989, Molecular Cloning).

Furthermore, on the basis of the isolated DNA sequence, and of the protein sequence which it encodes, it is possible to design oligonucleotides which can be used to amplify homologous nucleic acid sequences by means of the polymerase chain reaction (PCR).

Another possibility of isolating homologous proteins consists in detecting them using specific antibodies which are directed against the protein, or parts thereof, which is/are encoded by the sequence of the present invention (e.g. peptide antibodies).

DESCRIPTION OF THE MOST IMPORTANT SEQUENCES AND FIGURES

SEQ ID No:1: Nucleotide sequence of the delta-6-desaturase-encoding cDNA for the *Tetrahymena thermophila* delta-6-desaturase. Start and stop codons are emphasized.

SEQ ID NO:2: The protein sequence of the *Tetrahymena* delta-6-desaturase which is deduced from SEQ ID No.: 1 taking into consideration the special ciliate codon usage (Wuitschick J D, Karrer K M (1999) or CUTG (codon usage tabulated from Genbank).

SEQ ID No:3: Genomic nucleotide sequence for the *Tetrahymena thermophila* delta-6-desaturase.

FIG. 1: Diagram of PUFA biosynthesis.

FIG. 2: Result of a BLASTP database comparison of the protein sequence as depicted in SEQ ID No.: 2 with protein databases.

FIG. 3: Alignment of the protein sequence depicted in SEQ ID No.: 2 with known desaturases.

FIG. 4: Multiple alignment of the *Tetrahymena* polypeptide sequence depicted in SEQ ID No.: 2 with known desaturases. The histidine boxes and the conserved HPGG motif from the cytochrome b5 domain are underlined.

Figure 5:
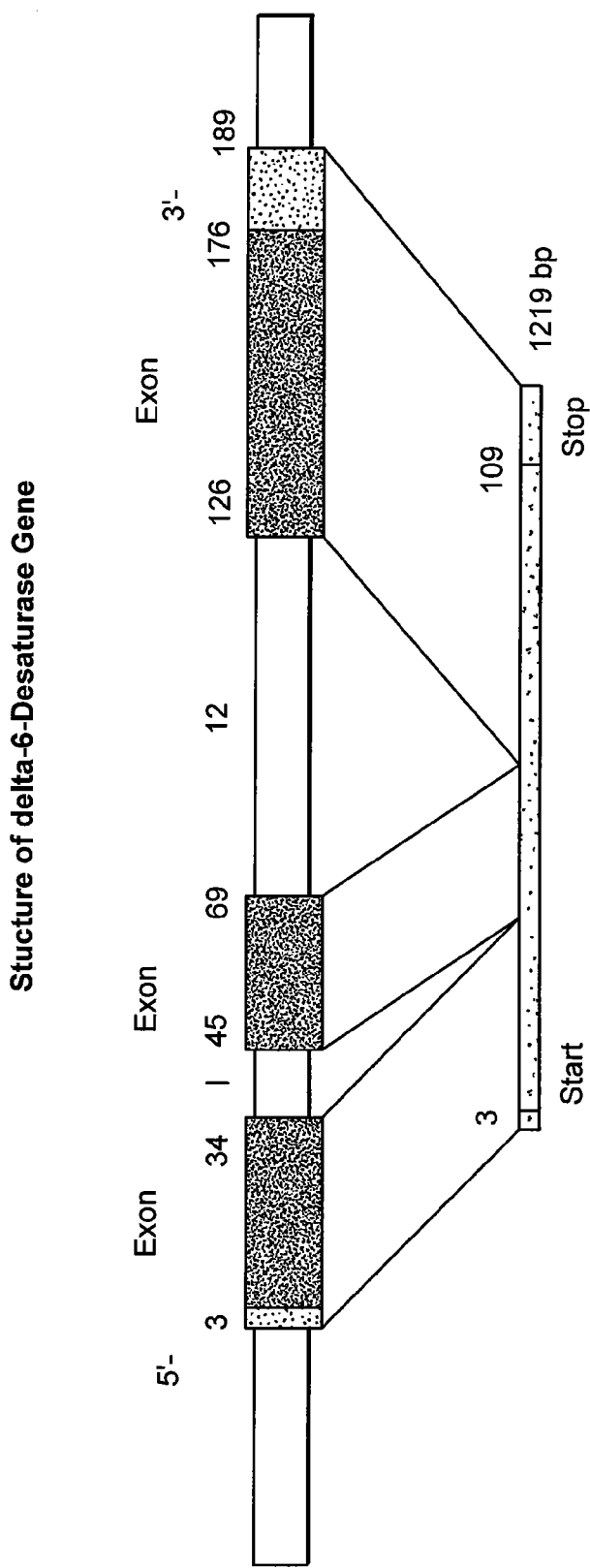

FIG. 5: Diagram of the structure of the *Tetrahymena* delta-6-desaturase gene as depicted in SEQ ID No.: 1 and 3.

Figure 6:
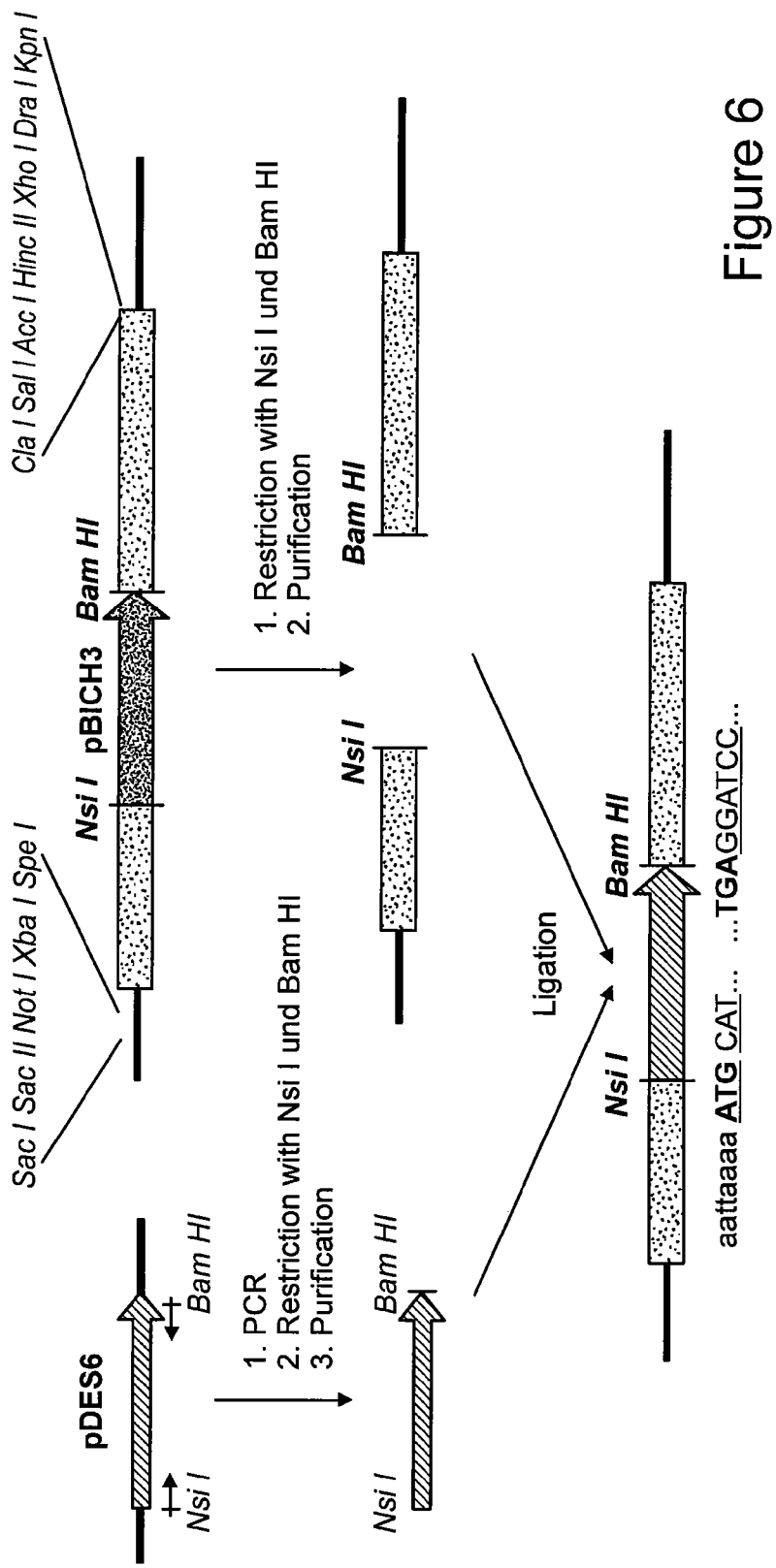

FIG. 6: Preparation of the pBDES6 delta-6-desaturase expression construct.

Figure 7:
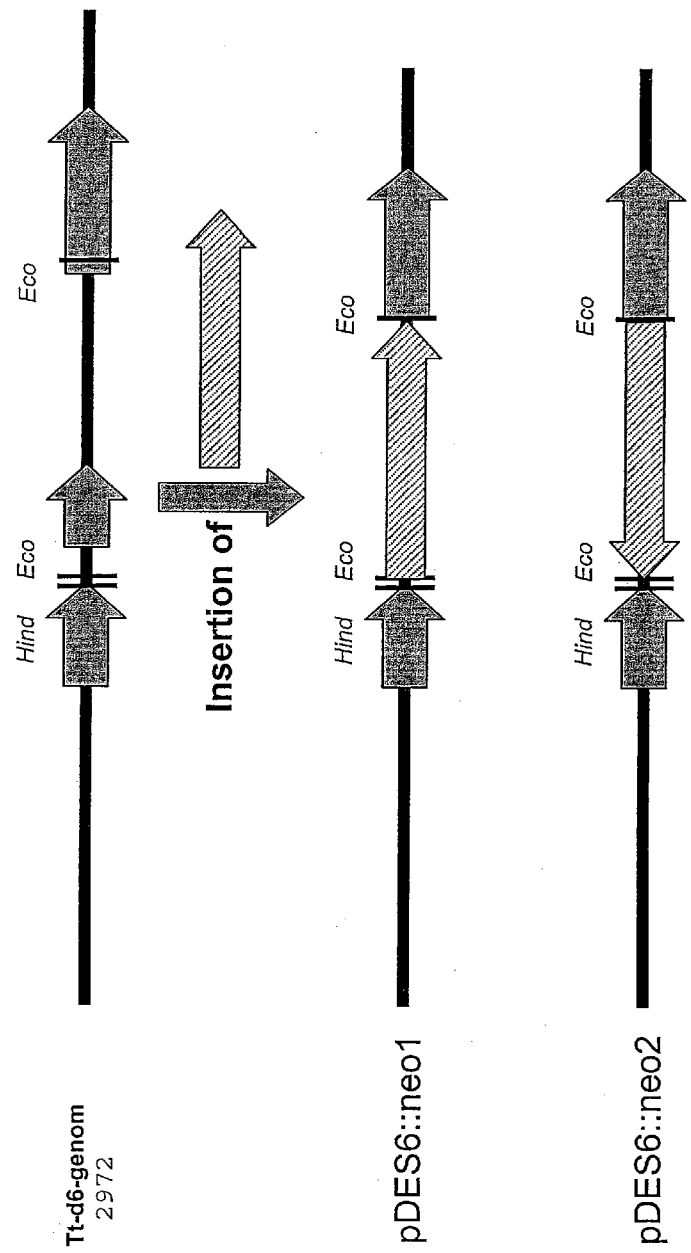

FIG. 7: Preparation of the pgDES6::neo knockout constructs.

Figure 8:
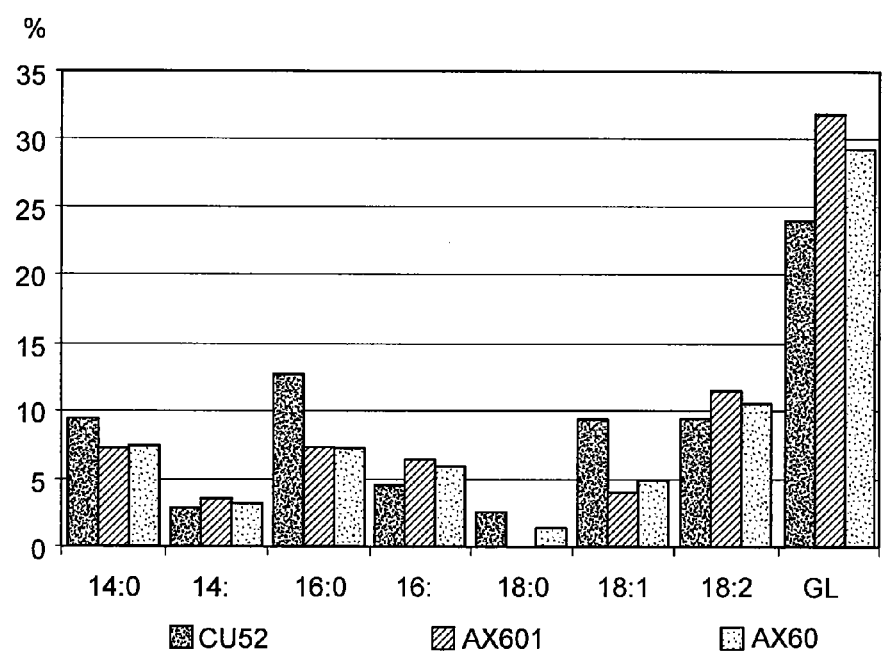

FIG. 8: Comparison of the fatty acid spectrum (main fatty acids) of the *Tetrahymena* pBDES6 transformants (AX601 and AX604) with that of the *Tetrahymena* wild-type strain (CU522).

EXAMPLES

The following examples serve to explain the invention without restricting it to these examples.

Example 1

Organisms and Culture Conditions

*Tetrahymena thermophila* (strains B1868 VII, B2086 II, B*VI, CU427, CU428 and CU522, kindly provided by Dr. J. Gaertig, University of Georgia, Athens, Ga., USA) were cultured in modified SPP medium (2% proteose peptone, 0.1% yeast extract, 0.2% glucose, 0.003% Fe-EDTA (Gaertig et al. (1994) PNAS 91:4549–4553)) or skimmed milk medium (2% skimmed milk powder, 0.5% yeast extract, 1% glucose, 0.003% Fe-EDTA) or MYG medium (2% skimmed milk powder, 0.1% yeast extract, 0.2% glucose, 0.003 % Fe-EDTA) in the added presence of antibiotic solution (100

U of penicillin/ml, 100 µg of streptomycin/ml and 0.25 µg of amphotericin B/ml (SPPA medium)) at 30° C. in a volume of 50 ml in 250 ml Erlenmeyer flasks while shaking (150 rpm).

Plasmids and phages were replicated in *E. coli* XL1-Blue MRF', TOP10F' or JM109 and selected. The bacteria were cultured under standard conditions in LB or NZY medium containing antibiotics in standard concentrations (Sambrook et al. (1989) Molecular Cloning: A Laboratory Manual, Cold Spring Harbor Laboratory, Cold Spring, N.Y.).

Example 2

Preparing a *Tetrahymena thermophila* cDNA Library

*Tetrahymena thermophila* total RNA was isolated using the guanidine thiocyanate/phenol/chloroform method (Chomzynski & Sacchi (1987) Anal. Biochem. 161:156–159). The mRNA was isolated from the total RNA using Oligotex-dT beads (Qiagen). The cDNA was synthesized using the Stratagene ZAP Express cDNA Synthesis and Cloning Kit. After ligating on the EcoR I adapter and digesting with Xho I, the DNA was separated on an agarose gel and size-fractionated (S: 500–1500 bp, B: greater than 1500 bp). The DNA was isolated from the gel (Qiaquick gel extraction kit, QIAGEN) and ligated into ZAP Express vector, which had been cut with Eco RI and Xho I. The ligated DNA was packaged in vitro into phages (Stratagene Gigapack III Gold) and the phages were replicated in *E. coli* XL1-Blue MRF'. The S cDNA library contained approx. 5×55 clones having an average insert size of 1.1 kb, while the B cDNA library contained approx. $6 \times 10^4$ clones having an average insert size of 2 kb.

Example 3

RT-PCR Using Delta-6-Desaturase-Specific Primers

By comparing sequences of known desaturses, it was possible to identify conserved regions. While taking into consideration the special ciliate codon usage and/or *Tetrahymena* codon usage, it was possible to design PCR primers for the particularly strongly conserved amo acid regions WWKWNHNAHH (SEQ ID No.: 4) and GGLQFQIE-HHLFP (SEQ ID No.: 5) (Wuitschick J D, Karrer K M (1999) Analysis of genomic G+C content, codon usage, initiator codon context and translation termination sites in *Tetrahymena thermophila*. J. Eukaryot. Microbiol. 46(3): 239–47; Martindale (1989) J. Protozool. 36, 1:29–34, CUTG, (Codon Usage Tabulated from Genbank.

Primer 1 (sense): 5'-TGGTGGAARTGGAMNCAYAA-3', (SEQ ID No.: 6)

Primer 2 (antisense): 5'-CGDGGRAANARRTGRTGTTC-3' (SEQ ID No.: 7).

100 ng of isolated mRNA were employed for the first strand synthesis using AMV reverse transcriptase (Boehringer Mannheim). The reaction took place in accordance with the manufacturer's protocol in a volume of 20 µl: 50 mM tris-HCl (pH 8.5), 8 mM $MgCl_2$, 30 mM KCl, 1 mM DTT, 1 mM dNTPs, 2 pmol of oligo-DT anchor primer (5'-GACCACGCGTATCGATGTCGACT(16)V-3'; SEQ ID No.: 8), 2 units of AMV reverse transcriptase; 60 min at 55° C., and subsequently 10 min at 65° C. 1/10 of this first strand reaction was used for the PCR. The PCR took place in a volume of 25 µl containing: 1×Qiagen HotStarTaq PCR buffer (QIAGEN), pH 8.7 (20° C.), 10 pmol each of the delta-6-desaturase-specific primers, in each case 200 µM dNTPs, 1.5 mM $MgCl_2$, 1 unit of HotStarTaq polymerase (Qiagen). The PCR was carried out under the following conditions: initial denaturation at 95° C. for 15 min, with this being followed by 35 cycles consisting in each case of 94° C. for 30 sec, 45° C. for 30 sec and 72° C. for 1 min. In conclusion, 10 min at 72° C. The PCR fragments were ligated into the vector pCR 2.1 by means of T/A cloning (Invitrogen) and replicated in *E. coli* TOP10F' (Invitrogen). Plasmid DNA was isolated from positive clones (Qiaprep Spin, QIAGEN) and sequenced.

Example 4

Isolating the Complete Delta-6-Desaturase-Encoding cDNA

On the basis of the sequence which was determined in this way, new oligonucleotides were designed for the PCR:

Primer d6/1-F (sense): 5'-GGAATCACAATCAACAT-CATATGTTCAC-3' (SEQ ID No. 9) and

Primer d6/1-R (antisense): 5'-CTTCGTCCTTTAGAATGT-TGTTTGTGAAC-3' (SEQ ID No.: 10).

The complete delta-6-desaturase-encoding cDNA was isolated by PCR from the cDNA library using these primers in combination with vector-specific primers (T3 and T7). 2 µl ($10^5$ pfu/µl) of the cDNA library were used for a PCR (see above). Departing from the abovementioned conditions, the PCR took place in accordance with the following protocol: denaturation for 15 min at 95° C., with this being followed by 35 cycles consisting of 20 sec at 94° C., 20 sec at 57° C. and 1 min at 72° C. In conclusion, 10 min at 72° C. The PCR products were sequenced using the primers which were also employed for the PCR. On the basis of the sequence information which was obtained in this way, a new primer which lay at the 5' end of the cDNA sequence was designed:

Primer d6-5'-F: AGTAAGCAAACTAAATTTAAAAAA-CAAGC (SEQ ID No.: 11)

Using this primer in combination with a vector-specific primer, it was possible to amplify and isolate the complete cDNA sequence by means of PCR (PCR conditions, see above). The plasmid pDES6 was obtained by cloning this PCR product into the vector pCR 2.1.

Example 5

Preparing a *Tetrahymena thermophila* Genomic DNA Library

Genomic DNA was isolated by the urea method (Gaertig et al. 1994) from *Tetrahymena* and cut with Eco R I. The cut DNA was ligated into a lambda vector (Zap Express, Stratagene) which had likewise been cut with Eco R I. Further processing corresponded to the procedure described in the case of the cDNA library.

Example 6

Isolating the Delta-6-Desaturase Genomic Sequence

The genomic sequence for delta-6-desaturase was investigated by means of PCR. In the first place, a PCR product of approx. 2200 bp in size, which contained the entire coding sequence and introns, was generated from genomic DNA using primers from the 5' and 3' ends of the cDNA:

d6-5'-F: AGTAAGCAAACTAAATTTAAAAAACAAGC (SEQ ID No.:12)

d6-3'-R: GGTCCTTCATGAATCTTAAGGTTCCACTTC (SEQ ID No.:13)

The Genome Walker System (Clonetech) was used to isolate flanking sequences of the delta-6-desaturase gene. Using the universal primers from this system and specific primers based on the delta-6-desaturase sequence which had been determined, i.e.

d6-5'-R: CTTAAGTCTTATCAACTCCCATAATGC (SEQ ID No.: 14)

d6-3'-F: GAAGTGGAACCTTAAGATTCATGAAGGACC (SEQ ID No.:15) it was possible to isolate flanking regions of the *Tetrahymena* delta-6-desaturase gene. The complete structure of the genomic sequence is depicted in FIG. 5.

Example 7

Preparing the pBDES6 Expression Constructs

The vector pBICH3 (Gaertig et al. 1999 Nature Biotech. 17:462-465) contains the sequence encoding the Ichthyophthirius I antigen (G1) preprotein flanked by noncoding, regulatory sequences of the *Tetrahymena thermophila* BTU1 gene. A modified plasmid (pBICH3-Nsi), containing an Nsi I cleavage site at the start (kindly provided by J. Gaertig, University of Georgia, Athens, Ga., USA), was used to prepare the delta-6-desaturase expression construct pBDES6. For this, PCR was used to insert Nsi I and Bam HI cleavage sites at the start and stop of the sequences encoding the *Tetrahymena* delta-6-desaturase. Isolated plasmids which contain the complete cDNA sequences for the delta-6-desaturase (pDES6) were employed as the template for the PCR. The primers D6-Nsi-F: 5'-GCATTATGCATGTTGATAAGACTTAAGAAG-3' (SEQ ID No.: 16)

D6-Bam-R: 5'-TATGGATCCTCAAAGGTGAGATTTTTCAAAAATAG-3, (SEQ ID No.: 17)

generated PCR products which contained the complete sequence coding for the delta-6-desaturase flanked by Nsi I and Bam HI cleavage sites. The PCR products, and the plasmid pBICH3-Nsi, were cut with the restriction enzymes Nsi I and Bam HI, purified on an agarose gel and ligated together (see the plasmid construction figure). The resulting pBDES6 expression constructs contained the complete delta-6-desaturase-encoding sequence inserted, in a correct reading frame, into the regulatory sequences of the BTU1 gene (see FIG. 6). For transforming *Tetrahymena*, the constructs were linearized by being digested with the restriction enzymes Xba I and Sal I. When successful transformation occurred, the BTU1 gene was replaced with these constructs by homologous recombination, resulting in the cells becoming resistant to paclitaxel.

Example 8

Determining the Fatty Acid Spectrum of the Transformants

The fatty acid spectrum was determined using gas chromatographs (HP GC 6890) having a flame ionization detector (Hewlett-Packard Company, Wilmington, USA). The column employed was an FFAP (free fatty acid phase) Permbond (Macherey & Nagel GmbH, Düren). The fatty acids were identified by comparison with the retention times for fatty acid methyl ester standards. It was possible to determine the concentration of the fatty acids in the samples on the basis of the known concentrations of the standard.

For determining the fatty acid spectrum, the isolated transformants were cultured for 24–96 h in MYG medium at 30° C. and 150 rpm. 50 ml of the culture were centrifuged at 1500 g for 15 min, after which the supernatant was discarded and the pellet was frozen at −80° C. and subsequently freeze-dried. 50 mg of the lyophilized sample were weighed out and treated with 1 ml of 20 % methanolic HCl and 1 ml of methanolic standard solution (1 mg/ml). In order to release the fatty acids and transesterify them into fatty acid methyl esters, the samples were agitated at 60° C. for two hours in sealed test tubes in a waterbath and then cooled down to room temperature. 1 ml of an aqueous, saturated solution of sodium hydrogen carbonate was then added to neutralize the sample, with the sample being carefully mixed. The fatty acid methyl esters were extracted by adding n-hexane. The preparation was subsequently thoroughly mixed vigorously and phase separation was achieved by centrifuging at 4300 rpm for 2 min. About ⅔ of the upper, organic phase was removed and 1 μl of the sample was injected onto the GC column and analyzed.

TABLE 1

GLA content of the Tetrahymena pBDES6 transformants (AX601 and AX604) compared with that of the Tetrahymena wild-type strain (CU522), following 50 h of culture. The table gives the percentage content of GLA in the total fatty acid spectrum and the percentage difference in the transformants as compared with the untransformed Tetrahymena strain CU522.

| Strain (plasmid) | GLA area % | Difference compared with CU522 |
|---|---|---|
| CU522(−) | 24.0 | — |
| AX601 (pBDES6) | 31.7 | +32% |
| AX604 (pBDES6) | 29.3 | +22% |

TABLE 2

Comparison of the fatty acid spectrum (main fatty acids) of the Tetrahymena pBDES6 transformants (AX601 and AX604) with that of the Tetrahymena wild-type strain (CU522) following 50 h of culture. The table gives the percentage content of the main fatty acids in the total fatty acid spectrum and also the ratio of the unsaturated main fatty acids to the saturated main fatty acids.

| Fatty acids | Cu522(−) | AX601 (pBDES6) | AX604 (pBDES6) |
|---|---|---|---|
| C14:0 | 9.4 | 7.2 | 7.4 |
| C14:1 | 2.8 | 3.5 | 3.1 |
| C16:0 | 12.7 | 7.3 | 7.2 |
| C16:1 | 4.5 | 6.4 | 6 |
| C18:0 | 2.6 | — | 1.4 |
| C18:1 | 9.5 | 3.9 | 4.8 |
| C18:2 | 9.4 | 11.5 | 10.6 |
| GLA (C18:3) | 24 | 31.7 | 29.3 |
| unsaturated | 50.2 | 57 | 53.8 |
| saturated | 24.7 | 14.5 | 16 |
| unsaturated/ saturated | 2.03 | 3.93 | 3.36 |

Under these conditions, the transformants exhibited a content of GLA in the total fatty acid spectrum which was increased by 22–32% as compared with that of the untransformed strain CU522 (Table 1). In addition to the shift in the GLA content, the marked shift in the fatty acid spectrum toward a higher content of unsaturated fatty acids is also striking. In the transformants, the ratio of unsaturated to saturated (main) fatty acids is almost twice as high (Table 2).

Example 9

Preparing the Delta-6-Desaturase Knockout Construct pgDES6::neo

In order to prepare the knockout construct, a neo cassette from the plasmid p4T2-1ΔH3 (Gaertig et al. (1994) Nucl. Acids Res. 22:5391–5398) was inserted into the delta-6-desaturase genomic sequence. This neo cassette is composed of the neomycin resistance gene under the control of the *Tetrahymena* histone H4 promoter and the 3'-flanking sequence of the BTU2 gene. In *Tetrahymena*, this construct mediates resistance to paromomycin. The plasmid p4T2-1ΔH3 was cut with Eco RV/Sma I and the neo cassette fragment, of approx. 1.4 kb in size, was ligated into the *Tetrahymena* delta-6-desaturase genomic sequence contained in plasmid pgDES6, which had been cut with Eco RV (see FIG. 8). This resulted in the plasmid pgDES6::neo. When successful transformation occurred, the gene encoding the delta-6-desaturase was replaced with this construct by means of homologous recombination, resulting in the cells becoming resistant to paromomycin.

Example 10

Macronucleus Transformation of *Tetrahymena* Using the Desaturase Expression Construct pBDES6

$5 \times 10^6$ *Tetrahymena thermophila* cells (CU522) were employed for a transformation. The cells were cultured in 50 ml of SPPA medium at 30° C. in a 250 ml Erlenmeyer flask on a shaker at 150 rpm until the cell density had reached approx. $3–5 \times 10^5$ cells/ml. The cells were pelleted by centrifuging (1200 g) for 5 min and the cell pellet was resuspended in 50 ml of 10 mM tris-HCl (pH 7.5, and centrifuged as before. This washing step was repeated and the cells were resuspended, at a cell density of $3 \times 10^5$ cells/ml, in 10 mM tris-HCl (pH 7.5, plus antibiotics), after which they were transferred to a 250 ml Erlenmeyer flask and incubated at 30° C. for 16–20 h without shaking (starvation phase). Following the starvation phase, the cell count was determined once again, after which the cells were centrifuged as above and subsequently adjusted, with 10 mM tris-HCl (pH 7.5), to a concentration of $5 \times 10^6$ cells/ml. one ml of the cells was used for the transformation. The transformation was effected by means of microparticle were taken up in SSPA medium and incubated at 30° C. in an Erlenmeyer flask without shaking. After 3 h, Paclitaxel® was added to give a final concentration of 20 μM and the cells were transferred, in aliquots of 100 μl, to 96-well microtiter plates. The cells were incubated at 30° C. in a moist, darkened box. After 2–3 days, it was possible to identify Paclitaxel-resistant clones. Positive clones were transferred by inoculation into fresh medium containing 25 μM Paclitaxel. A complete "phenotypic assortment" (Gaertig & Kapler (1999)) was achieved by culturing the cells in increasing concentrations of Paclitaxel (up to 80 μM). In order to analyze the clones, cultures of approx. 4 ml were grown in SPPA containing Paclitaxel, after which the DNA was isolated (Jacek Gaertig et al. (1994) PNAS 91:4549–4553) and the DNA which was integrated into the BTU1 locus was amplified by means of PCR. The primers employed were the BTU1-specific primers BTU1-5'F (AAAAATAAAAAAGTTTGAAAAAAAACCTTC, approx. 50 bp upstream of the start codon, SEQ ID No.: 18) and BTU1 3'R (GTTTAGCTGACCGATTCAGTTC, 3 bp downstream of the stop codon, SEQ ID No.: 19). The PCR products were analyzed on a 1% agarose gel either in the uncut state or having been cut with Hind III or Eco RV (pBDES6) or Eco RI (pBDES9). Complete "phenotypic assortment" was verified by means of RT-PCR using the BTU1-specific primers (Gaertig & Kapler (1999)).

Example 11

Micronucleus and Macronucleus Transformation of *Tetrahymena* Using the Knockout Construct pgDES6::neo

*Tetrahymena* strains of differing pairing types (CU428 VII and B2086 II) were cultured separately in SPPA medium, at 30° C. and with shaking (150 rpm), in Erlenmeyer flasks. At a cell density of $3–5 \times 10^5$ cells/ml, the cells were centrifuged (1200 g) for 5 min at room temperature. The cells were washed three times with 50 ml of 10 mM tris-HCl (pH 7.5) and finally resuspended in 50 ml of 10 mM tris-HCl (pH 7.5), after which antibiotic solution was added. The cells were incubated at 30° C., without shaking, in Erlenmeyer flasks. After approx. 4 h, the two cultures were counted once again and diluted with 10 mM tris-HCl (pH 7.5) to $3 \times 10^5$ cells/ml, after which they were incubated at 30° C. for a further 16–20 h. After this starvation phase, the same (absolute) number of cells from the two cultures were mixed in a 2 L Erlenmeyer flask. The cells were incubated at 30° C. (beginning of conjugation) and the efficiency of the conjugation was determined after 2 h. For the transformation to be successful, approx. 30% of the cells should be present as pairs at this time.

For the micronucleus transformation, in each case $1 \times 10^7$ conjugating cells ($5 \times 10^6$ pairs) were centrifuged, at 3 h, 3.5 h, 4 h and 4.5 h after the beginning of conjugation, at 1200 g for 5 min and the cell pellet was resuspended in 1 ml of 10 mM tris-HCl (pH 7.5).

For transforming the new macronucleus primordia, cells were centrifuged as above, at 11 h after the beginning of conjugation, and resuspended in tris-HCl. The transformation was effected by means of microparticle bombardment (see above).

For culturing the delta-6-desaturase knockout mutants, 200 μg of borage oil (20–25% GLA; SIGMA)/ml were added to the medium.

It was possible to identify transformed cells by selecting for paromomycin resistance. In the case of transforming the micronucleus, paromomycin (final concentration, 100 μg/ml) was added at 11 h after beginning the conjugation and the cells were apportioned on 96-well microtiter plates in aliquots of 100 μl. The cells were incubated in a moist box at 30° C. It was possible to identify resistant clones after 2–3 days. It was possible to distinguish genuine micronucleus transformants on the basis of the resistance of macronucleus transformants to 6-methylpurine. When the macronucleus was transformed, paromomycin (final concentration, 100 μg/ml) was added approx. 4 h after the transformation and the cells were apportioned on 96-well microtiter plates in aliquots of 100 μl. The cells were incubated in a moist box at 30° C. It was possible to identify resistant clones after 2–3 days. Positive clones were transferred by inoculation into fresh medium containing 120 μg of paromomycin/ml. A complete "phenotypic assortment" (Gaertig & Kapler (1999)) was achieved after a few generations by culturing the cells in this high paromomycin concentration.

By crossing the micronucleus transformants with a B*VI strain, it was possible to generate homozygous knockout mutants (Bruns & Cassidy-Hanley, Methods in Cell Biology, Volume 62 (1999) 229–240).

Example 12

Biolistic Transformation (Microparticle Bombardment)

*Tetrahymena thermophila* were transformed by means of biolistic transformation, as described in Bruns & Cassidy-Hanley (Methods in Cell Biology, Volume 62 (1999) 501–502); Gaertig et al. (1999) Nature Biotech. 17: 462–465) or Cassidy-Hanley et al. ((1997) Genetics 146: 135–147). The operation of the Biolistic® PDS-1000/He Particle Delivery System (BIO-RAD) is detailed in the accompanying manual.

For the transformation, 6 mg of gold particles 10.6 μm: BIO-RAD) are loaded with 10 μg of linearized plasmid DNA (Sanford et al. (1991) Biotechniques 3:3–16; Bruns & Cassidy-Hanley (1999) Methods in Cell Biology, Volume 62: 501–512).

Preparation of the gold particles: 60 mg of the 0.6 μm gold particles (Biorad) were resuspended in 1 ml of ethanol. For this, the particles were vigorously mixed 3 times, for in each case 1–2 min, on a vortex. Subsequently, the particles were centrifuged (10000 g) for 1 min and the supernatant was carefully removed using a pipette. The gold particles were resuspended in 1 ml of sterile water and centrifuged as above. This washing step was repeated once and the particles were resuspended in 1 ml of 50% glycerol and stored at −20° C. in aliquots of 100 μl.

Preparing the transformation: The macrocarrier holder, macrocarrier and stopscreens were stored for several hours in 100% ethanol, while the rupture disks were stored in isopropanol. A macrocarrier was subsequently inserted into the macrocarrier holder and dried in air.

Loading the gold particles with DNA: All the steps were carried out at 4° C. Gold particles, prepared vector, 2.5 M $CaCl_2$, 1 M spermidine and 70% and 100% ethanol were cooled on ice. 10 μl of the linearized vector DNA (1 μg/ml) were added to 100 μl of prepared gold particles and the mixture was carefully vortexed for 10 sec. Subsequently, 100 μl of 2.5 M $CaCl_2$ were firstly added, after which the mixture was vortexed for 10 sec, and 40 μl of 1 M spermidine were then added and the mixture was carefully vortexed for 10 min. After adding 200 μl of 70% ethanol, the particles were vortexed for 1 min and then centrifuged at 10000 g for 1 min. The pellet was resuspended in 20 μl of 100% ethanol, centrifuged and then resuspended in 35 μl of 100% ethanol.

The particles which had been prepared in this way were carefully added, using a pipette, to the center of a macrocarrier. The macrocarrier was subsequently stored in a box containing hygroscopic silica gel until the transformation took place.

Transformation: One ml of the prepared cells (see above) was added to the middle of a round filter, which had been moistened with 10 mM tris-HCl (pH 7.5), in a Petri dish and inserted into the lowest slide-in ledge in the Biolistic® PDS-1000/He Particle Delivery System transformation chamber. The transformation took place using the prepared gold particles at a pressure of 900 psi (two 450 psi rupture disks) and under a vacuum of 27 inches of Hg in the transformation chamber. The cells were then immediately transferred to an Erlenmeyer flask containing 50 ml of SPPA medium and incubated at 30° C. without shaking.

---

The invention claimed is:

1. An isolated nucleic acid encoding *Tetrahymena* delta-6-desaturase as shown in SEQ ID NO:2.

2. An isolated nucleic acid as claimed in claim 1, which is obtained from *Tetrahymena thermophila*.

3. An isolated nucleic acid as claimed in claim 1 which is DNA.

4. An isolated nucleic acid as claimed in claim 1, which is a DNA comprising a nucleic acid sequence as depicted in SEQ ID. NO.: 1 from position 33 to position 1091.

5. An isolated nucleic acid as claimed in claim 1 comprising one or more noncoding sequences.

6. A vector comprising a nucleic acid encoding *Tetrahymena* delta-6-desaturase as shown in SEQ ID NO:2.

7. The vector of claim 6, wherein the nucleic acid is functionally combined with a constitutive promoter.

8. A process for preparing a nucleic acid encoding *Tetrahymena* delta-6-desaturase as shown in SEQ ID NO:2, the process comprising chemically synthesizing the nucleic acid.

9. A transgenic, nonhuman organism comprising a nucleic acid encoding *Tetrahymena* delta-6-desaturase as shown in SEQ ID NO:2.

10. The transgenic organism of claim 9 in which the transgenic organism is a plant or a ciliate.

11. The isolated nucleic acid of claim 3 in which the DNA is double-stranded DNA.

12. The vector of claim 6 in which the vector is an expression vector.

13. The vector of claim 6 wherein the nucleic acid is functionally combined with an inducible promoter.

14. The vector of claim 7 wherein the nucleic acid is functionally combined with an inducible promoter.

15. The vector of claim 7 wherein the nucleic acid further comprises a termination signal.

16. The vector of claim 13 wherein the nucleic acid further comprises a termination signal.

17. The vector of claim 14 wherein the nucleic acid further comprises a termination signal.

18. A process for preparing a nucleic acid encoding *Tetrahymena* delta-6-desaturase as shown in SEQ ID NO:2, the process comprising isolating the nucleic acid from a gene library using a probe which hybridizes to the nucleic acid.

19. The process of claim 12 in which the expression vector is in a host organism.

20. A method of enriching delta-6-desaturase dependent fatty acids in ciliates, the method comprising:

inserting a vector comprising a nucleic acid encoding *Tetrahymena* delta-6-desaturase as shown in SEQ ID NO:2 into a ciliate; and expressing the nucleic acid to enrich delta-6-desaturase dependent fatty acids in the ciliate.

21. The method of claim 20 in which the vector comprises at least one inducible promoter.

22. An isolated nucleic acid as claimed in claim 1 which is RNA.

23. An isolated nucleic acid as claimed in claim 1, which is obtained from a ciliate.

* * * * *